United States Patent
Du

(10) Patent No.: US 11,524,932 B2
(45) Date of Patent: Dec. 13, 2022

(54) LIPIDS FOR USE IN LIPID NANOPARTICLE FORMULATIONS

(71) Applicant: ACUITAS THERAPEUTICS, INC., Vancouver (CA)

(72) Inventor: Xinyao Du, Richmond (CA)

(73) Assignee: Acuitas Therapeutics, Inc., Vancouver (CA)

(*) Notice: Subject to any disclaimer, the term of this patent is extended or adjusted under 35 U.S.C. 154(b) by 0 days.

(21) Appl. No.: 16/638,731

(22) PCT Filed: Aug. 17, 2018

(86) PCT No.: PCT/US2018/000317
§ 371 (c)(1),
(2) Date: Feb. 12, 2020

(87) PCT Pub. No.: WO2019/036030
PCT Pub. Date: Feb. 21, 2019

(65) Prior Publication Data
US 2021/0122703 A1    Apr. 29, 2021

Related U.S. Application Data

(60) Provisional application No. 62/547,043, filed on Aug. 17, 2017.

(51) Int. Cl.
| | |
|---|---|
| *C07C 229/06* | (2006.01) |
| *A61K 9/51* | (2006.01) |
| *A61K 31/7088* | (2006.01) |
| *A61K 38/00* | (2006.01) |
| *A61K 47/18* | (2017.01) |
| *A61K 47/24* | (2006.01) |
| *A61K 47/28* | (2006.01) |
| *C12N 15/113* | (2010.01) |

(52) U.S. Cl.
CPC .......... *C07C 229/06* (2013.01); *A61K 9/5123* (2013.01); *A61K 31/7088* (2013.01); *A61K 38/00* (2013.01); *A61K 47/18* (2013.01); *A61K 47/24* (2013.01); *A61K 47/28* (2013.01); *C12N 15/113* (2013.01); *C12N 2310/11* (2013.01); *C12N 2320/32* (2013.01)

(58) Field of Classification Search
CPC ...... A61K 38/00; A61K 47/18; A61K 47/543; C12N 15/113; C12N 2310/11; C12N 2320/32
USPC ...... 424/9.1; 435/6.1, 91.1, 91.31, 455, 458; 514/44 A, 44 R; 536/23.1, 24.5
See application file for complete search history.

(56) References Cited

U.S. PATENT DOCUMENTS

| | | |
|---|---|---|
| 2,856,420 A | 10/1958 | Crawford, Jr. |
| 3,340,299 A | 9/1967 | Weintraub et al. |
| 3,729,564 A | 4/1973 | Chang et al. |
| 3,931,430 A | 1/1976 | Tada et al. |
| 3,951,581 A | 4/1976 | Nakayama et al. |
| 4,121,898 A | 10/1978 | Kirschnek et al. |
| 4,491,583 A | 1/1985 | Cronin et al. |
| 4,639,468 A | 1/1987 | Roncucci et al. |
| 5,705,385 A | 1/1998 | Bally et al. |
| 5,756,785 A | 5/1998 | O'Lenick, Jr. |
| 5,919,743 A | 7/1999 | O'Lenick, Jr. |
| 5,965,542 A | 10/1999 | Wasan et al. |
| 5,976,567 A | 11/1999 | Wheeler et al. |
| 5,981,501 A | 11/1999 | Wheeler et al. |
| 6,013,813 A | 1/2000 | O'Lenick, Jr. |
| 6,034,137 A | 3/2000 | Belloni et al. |
| 6,077,509 A | 6/2000 | Weiner et al. |
| 6,107,286 A | 8/2000 | Byk et al. |
| 6,300,321 B1 | 10/2001 | Scherman et al. |
| 6,333,433 B1 | 12/2001 | Banerjee et al. |
| 6,410,328 B1 | 6/2002 | Maclachlan et al. |
| 6,458,381 B1 | 10/2002 | Sourovoi et al. |
| 6,534,484 B1 | 3/2003 | Wheeler et al. |
| 6,586,410 B1 | 7/2003 | Wheeler et al. |
| 6,620,794 B1 | 9/2003 | O'Lenick, Jr. et al. |
| 6,815,432 B2 | 11/2004 | Wheeler et al. |
| 6,858,224 B2 | 2/2005 | Wheeler et al. |
| 6,986,902 B1 | 1/2006 | Chen et al. |
| 7,112,337 B2 | 9/2006 | Huang et al. |
| 7,470,781 B2 | 12/2008 | Crouzet et al. |
| 7,745,651 B2 | 6/2010 | Heyes et al. |
| 7,799,565 B2 | 9/2010 | MacLachlan et al. |
| 7,803,397 B2 | 9/2010 | Heyes et al. |
| 7,811,602 B2 | 10/2010 | Cullis et al. |

(Continued)

FOREIGN PATENT DOCUMENTS

| | | |
|---|---|---|
| CN | 102604115 A | 7/2012 |
| CN | 104876831 A | 9/2015 |
| EP | 1 083 232 B1 | 2/2005 |
| GB | 1 277 947 A | 6/1972 |
| JP | S45-38429 B | 12/1970 |

(Continued)

OTHER PUBLICATIONS

U.S. Appl. No. 16/608,610, filed Oct. 25, 2019.

(Continued)

*Primary Examiner* — Jane J Zara
(74) *Attorney, Agent, or Firm* — Seed IP Law Group LLP

(57) ABSTRACT

Compounds are provided having the following structure (I) or a pharmaceutically acceptable salt, tautomer or stereoisomer thereof, wherein X, Y, $L^1$, $L^2$, $L^3$, $G^1$, $G^2$ and $G^3$ are as defined herein. Use of the compounds as a component of lipid nanoparticle formulations for delivery of a therapeutic agent, compositions comprising the compounds and methods for their use and preparation are also provided.

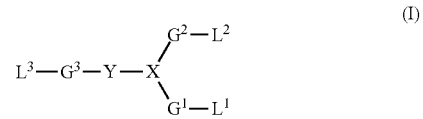

24 Claims, No Drawings

(56) References Cited

U.S. PATENT DOCUMENTS

| | | |
|---|---|---|
| 7,901,708 B2 | 3/2011 | MacLachlan et al. |
| 7,982,027 B2 | 7/2011 | MacLachlan et al. |
| 8,034,376 B2 | 10/2011 | Manoharan et al. |
| 8,158,601 B2 | 4/2012 | Chen et al. |
| 8,278,036 B2 | 10/2012 | Kariko et al. |
| 8,283,333 B2 | 10/2012 | Yaworski et al. |
| 8,329,070 B2 | 12/2012 | MacLachlan et al. |
| 8,466,122 B2 | 6/2013 | Heyes et al. |
| 8,569,256 B2 | 10/2013 | Heyes et al. |
| 8,575,123 B2 | 11/2013 | Manoharan et al. |
| 8,642,076 B2 | 2/2014 | Manoharan et al. |
| 8,691,750 B2 | 4/2014 | Constien et al. |
| 8,722,082 B2 | 5/2014 | Manoharan et al. |
| 8,748,089 B2 | 6/2014 | Kariko et al. |
| 8,754,062 B2 | 6/2014 | De Fougerolles et al. |
| 8,802,644 B2 | 8/2014 | Chen et al. |
| 8,822,668 B2 | 9/2014 | Yaworski et al. |
| 8,835,108 B2 | 9/2014 | Kariko et al. |
| 9,012,498 B2 | 4/2015 | Manoharan et al. |
| 9,139,554 B2 | 9/2015 | Hope et al. |
| 9,352,042 B2 | 5/2016 | Heyes et al. |
| 9,604,908 B2 | 3/2017 | Stanton et al. |
| 9,682,922 B2 | 6/2017 | Manoharan et al. |
| 9,737,619 B2 | 8/2017 | Ansell et al. |
| 9,738,593 B2 | 8/2017 | Ansell et al. |
| 9,750,824 B2 | 9/2017 | Kariko et al. |
| 9,795,566 B2 | 10/2017 | Oya et al. |
| 10,106,490 B2 | 10/2018 | Du |
| 10,144,725 B2 | 12/2018 | Brown |
| 10,166,298 B2 | 1/2019 | Ansell et al. |
| 10,221,127 B2 | 3/2019 | Du et al. |
| 10,682,374 B2 | 6/2020 | Dong et al. |
| 10,723,692 B2 | 7/2020 | Ansell et al. |
| 11,040,112 B2 | 6/2021 | Ansell et al. |
| 11,168,051 B2 | 11/2021 | Du et al. |
| 11,357,856 B2 | 6/2022 | Ansell et al. |
| 2002/0062044 A1 | 5/2002 | Banerjee et al. |
| 2003/0031704 A1 | 2/2003 | Huang et al. |
| 2003/0153081 A1 | 8/2003 | Tagawa et al. |
| 2004/0142025 A1 | 7/2004 | MacLachlan et al. |
| 2004/0142474 A1 | 7/2004 | Mahato et al. |
| 2005/0064595 A1 | 3/2005 | MacLachlan et al. |
| 2005/0250723 A1 | 11/2005 | Hoerr et al. |
| 2006/0100177 A1 | 5/2006 | Nishimura et al. |
| 2006/0188490 A1 | 8/2006 | Hoerr et al. |
| 2007/0042031 A1 | 2/2007 | MacLachlan et al. |
| 2008/0025944 A1 | 1/2008 | Hoerr et al. |
| 2008/0249296 A1 | 10/2008 | Chung et al. |
| 2009/0023718 A1 | 1/2009 | Miller et al. |
| 2009/0209037 A1 | 8/2009 | Tagawa et al. |
| 2009/0247608 A1 | 10/2009 | Manoharan et al. |
| 2009/0324584 A1 | 12/2009 | Hoerr et al. |
| 2010/0189729 A1 | 7/2010 | Hoerr et al. |
| 2010/0203076 A1 | 8/2010 | Fotin-Mleczek et al. |
| 2010/0285112 A1 | 11/2010 | Novobrantseva et al. |
| 2010/0305196 A1 | 12/2010 | Probst et al. |
| 2011/0045473 A1 | 2/2011 | De Fougerolles et al. |
| 2011/0091525 A1 | 4/2011 | Heyes et al. |
| 2011/0097720 A1 | 4/2011 | Ciufolini et al. |
| 2011/0250225 A1 | 10/2011 | Fotin-Mleczek et al. |
| 2011/0256175 A1 | 10/2011 | Hope et al. |
| 2011/0262527 A1 | 10/2011 | Heyes et al. |
| 2011/0300205 A1 | 12/2011 | Geall et al. |
| 2011/0305770 A1 | 12/2011 | Zhao et al. |
| 2011/0311582 A1 | 12/2011 | Manoharan et al. |
| 2011/0311583 A1 | 12/2011 | Manoharan et al. |
| 2012/0009222 A1 | 1/2012 | Nguyen et al. |
| 2012/0021043 A1 | 1/2012 | Kramps et al. |
| 2012/0027796 A1 | 2/2012 | Manoharan et al. |
| 2012/0027803 A1 | 2/2012 | Manoharan et al. |
| 2012/0046478 A1 | 2/2012 | Manoharan et al. |
| 2012/0058144 A1 | 3/2012 | Manoharan et al. |
| 2012/0058188 A1 | 3/2012 | Manoharan et al. |
| 2012/0095075 A1 | 4/2012 | Manoharan et al. |
| 2012/0101148 A1 | 4/2012 | Aking et al. |
| 2012/0128760 A1 | 5/2012 | Manoharan et al. |
| 2012/0172411 A1 | 7/2012 | Heyes et al. |
| 2012/0183602 A1 | 7/2012 | Chen et al. |
| 2012/0225434 A1 | 9/2012 | Ciufolini et al. |
| 2012/0244207 A1 | 9/2012 | Fitzgerald et al. |
| 2012/0251618 A1 | 10/2012 | Schrum et al. |
| 2012/0264810 A1 | 10/2012 | Lin et al. |
| 2012/0276209 A1 | 11/2012 | Cullis et al. |
| 2012/0295832 A1 | 11/2012 | Constien et al. |
| 2013/0017223 A1 | 1/2013 | Hope et al. |
| 2013/0022649 A1 | 1/2013 | Yaworski et al. |
| 2013/0064894 A1 | 3/2013 | Martin et al. |
| 2013/0108685 A1 | 5/2013 | Kuboyama et al. |
| 2013/0122104 A1 | 5/2013 | Yaworski et al. |
| 2013/0123338 A1 | 5/2013 | Heyes et al. |
| 2013/0129754 A1 | 5/2013 | Thess et al. |
| 2013/0129811 A1 | 5/2013 | Kuboyama et al. |
| 2013/0259879 A1 | 10/2013 | Baumhof et al. |
| 2013/0261172 A1 | 10/2013 | Kariko et al. |
| 2013/0266640 A1 | 10/2013 | de Fougerolles et al. |
| 2013/0280283 A1 | 10/2013 | Lorenz et al. |
| 2013/0280305 A1 | 10/2013 | Kuboyama et al. |
| 2013/0295043 A1 | 11/2013 | Kallen et al. |
| 2013/0323269 A1 | 12/2013 | Manoharan et al. |
| 2013/0336998 A1 | 12/2013 | Kallen et al. |
| 2013/0338210 A1 | 12/2013 | Manoharan et al. |
| 2014/0044772 A1 | 2/2014 | MacLachlan et al. |
| 2014/0121393 A1 | 5/2014 | Manoharan et al. |
| 2014/0134260 A1 | 5/2014 | Heyes et al. |
| 2014/0179761 A1 | 6/2014 | Manoharan et al. |
| 2014/0256785 A1 | 9/2014 | Manoharan et al. |
| 2014/0294937 A1 | 10/2014 | MacLachlan et al. |
| 2014/0295449 A1 | 10/2014 | Ciufolini et al. |
| 2014/0308304 A1 | 10/2014 | Manoharan et al. |
| 2014/0323548 A1 | 10/2014 | Budzik et al. |
| 2015/0037326 A1 | 2/2015 | Butler-Ransohoff et al. |
| 2015/0050302 A1 | 2/2015 | Thess |
| 2015/0057340 A1 | 2/2015 | Thess et al. |
| 2015/0093413 A1 | 4/2015 | Thess et al. |
| 2015/0118183 A1 | 4/2015 | Baumhof |
| 2015/0118264 A1 | 4/2015 | Baumhof et al. |
| 2015/0165006 A1 | 6/2015 | Thess et al. |
| 2015/0184195 A1 | 7/2015 | Thess et al. |
| 2015/0203446 A1 | 7/2015 | Manoharan et al. |
| 2015/0218554 A1 | 8/2015 | Thess |
| 2015/0306249 A1 | 10/2015 | Baumhof et al. |
| 2016/0009637 A1 | 1/2016 | Manoharan et al. |
| 2016/0095924 A1 | 4/2016 | Hope et al. |
| 2016/0130345 A1 | 5/2016 | Fotin-Mleczek et al. |
| 2016/0166668 A1 | 6/2016 | Kallen et al. |
| 2016/0166678 A1 | 6/2016 | Kallen et al. |
| 2016/0166710 A1 | 6/2016 | Baumhof |
| 2016/0166711 A1 | 6/2016 | Schnee et al. |
| 2016/0168207 A1 | 6/2016 | Kramps et al. |
| 2016/0235864 A1 | 8/2016 | Schlake et al. |
| 2016/0304883 A1 | 10/2016 | Grund et al. |
| 2016/0361411 A1 | 12/2016 | Gindy et al. |
| 2017/0029847 A1 | 2/2017 | Thess |
| 2017/0252430 A1 | 9/2017 | Fotin-Mleczek et al. |
| 2017/0266292 A1 | 9/2017 | Luo et al. |
| 2017/0326225 A1 | 11/2017 | Rauch et al. |
| 2018/0044687 A1 | 2/2018 | Thess et al. |
| 2018/0125952 A1 | 5/2018 | Fotin-Mleczek et al. |
| 2018/0126003 A1 | 5/2018 | Hoerr |
| 2018/0148727 A1 | 5/2018 | Grund et al. |
| 2018/0185516 A1 | 7/2018 | Ansell et al. |
| 2018/0214537 A1 | 8/2018 | Mutzke et al. |
| 2018/0237786 A1 | 8/2018 | Schlake et al. |
| 2018/0296663 A1 | 10/2018 | Hipp et al. |
| 2018/0303925 A1 | 10/2018 | Weissman et al. |
| 2018/0312545 A1 | 11/2018 | Baumhof et al. |
| 2019/0022247 A1 | 1/2019 | Ansell et al. |
| 2019/0024096 A1 | 1/2019 | Schmid et al. |
| 2019/0160164 A1 | 5/2019 | Rauch et al. |
| 2019/0270697 A1 | 9/2019 | Ansell et al. |
| 2019/0274968 A1 | 9/2019 | Weissman et al. |
| 2019/0314524 A1 | 10/2019 | Ansell et al. |
| 2019/0358314 A1 | 11/2019 | Weissman et al. |
| 2019/0359556 A1 | 11/2019 | Du et al. |

(56) References Cited

U.S. PATENT DOCUMENTS

| | | |
|---|---|---|
| 2020/0046838 A1 | 2/2020 | Ansell et al. |
| 2020/0121809 A1 | 4/2020 | Hope et al. |
| 2020/0163878 A1 | 5/2020 | Baumhof et al. |
| 2020/0172472 A1 | 6/2020 | Du |
| 2020/0283372 A1 | 9/2020 | Du |
| 2021/0069336 A1 | 3/2021 | Dong et al. |
| 2021/0107861 A1 | 4/2021 | Ansell et al. |
| 2021/0122702 A1 | 4/2021 | Du |
| 2021/0128488 A1 | 5/2021 | Du |
| 2021/0251898 A1 | 8/2021 | Baumhof et al. |
| 2021/0395188 A1 | 12/2021 | Ansell |
| 2022/0040285 A1 | 2/2022 | Weissman et al. |
| 2022/0072155 A1 | 3/2022 | Ansell et al. |
| 2022/0081392 A1 | 3/2022 | Du et al. |
| 2022/0106257 A1 | 4/2022 | Gatenyo et al. |

FOREIGN PATENT DOCUMENTS

| | | | |
|---|---|---|---|
| JP | H05-331118 A | 12/1993 | |
| JP | H10-3643 A | 1/1998 | |
| JP | 2001-338416 A | 12/2001 | |
| JP | 2004-262867 A | 9/2004 | |
| JP | 4681425 B2 | 5/2011 | |
| JP | 2017-522376 A | 8/2017 | |
| JP | 2018-533573 A | 11/2018 | |
| JP | 2020-517694 A | 6/2020 | |
| WO | 87/07183 A1 | 12/1987 | |
| WO | 97/03939 A1 | 2/1997 | |
| WO | 98/16599 A1 | 4/1998 | |
| WO | 99/05094 A1 | 2/1999 | |
| WO | 99/33493 A1 | 7/1999 | |
| WO | 00/30444 A1 | 6/2000 | |
| WO | 01/07548 A1 | 2/2001 | |
| WO | 01/48233 A1 | 7/2001 | |
| WO | 03/053409 A1 | 7/2003 | |
| WO | 2005/060934 A1 | 7/2005 | |
| WO | 2006/138380 A1 | 12/2006 | |
| WO | 2007/024708 A2 | 3/2007 | |
| WO | 2009/132131 A1 | 10/2009 | |
| WO | 2010/042877 A1 | 4/2010 | |
| WO | 2010/048536 A2 | 4/2010 | |
| WO | 2010/054405 A1 | 5/2010 | |
| WO | 2010/054406 A1 | 5/2010 | |
| WO | 2010/057150 A1 | 5/2010 | |
| WO | 2010/062322 A2 | 6/2010 | |
| WO | 2010/088537 A2 | 8/2010 | |
| WO | 2011/075656 A1 | 6/2011 | |
| WO | 2011/141703 A1 | 11/2011 | |
| WO | 2011/141705 A1 | 11/2011 | |
| WO | 2011/143230 A1 | 11/2011 | |
| WO | 2011/153493 A2 | 12/2011 | |
| WO | 2012/000104 A1 | 1/2012 | |
| WO | 2012/016184 A2 | 2/2012 | |
| WO | 2012/019630 A1 | 2/2012 | |
| WO | 2012/068176 A1 | 5/2012 | |
| WO | 2012/133737 A1 | 10/2012 | |
| WO | 2013/014073 A1 | 1/2013 | |
| WO | 2013/016058 A1 | 1/2013 | |
| WO | 2013/044008 A2 | 3/2013 | |
| WO | 2013/059816 A1 | 4/2013 | |
| WO | 2013/086322 A1 | 6/2013 | |
| WO | 2013/086354 A1 | 6/2013 | |
| WO | 2013/086373 A1 | 6/2013 | |
| WO | 2013/143555 A1 | 10/2013 | |
| WO | 2014/008334 A1 | 1/2014 | |
| WO | 2014/028487 A1 | 2/2014 | |
| WO | 2014/089239 A1 | 6/2014 | |
| WO | 2014/153163 A1 | 9/2014 | |
| WO | 2014/160243 A1 | 10/2014 | |
| WO | 2014/160284 A1 | 10/2014 | |
| WO | 2015/074085 A1 | 5/2015 | |
| WO | 2015/123576 A2 | 8/2015 | |
| WO | 2015/130584 A2 | 9/2015 | |
| WO | 2015/164674 A1 | 10/2015 | |
| WO | 2015/177752 A1 | 11/2015 | |
| WO | 2015/199952 A1 | 12/2015 | |
| WO | 2016/010840 A1 | 1/2016 | |
| WO | 2016/014794 A1 | 1/2016 | |
| WO | 2017/004143 A1 | 1/2017 | |
| WO | WO-2017004143 A1 * | 1/2017 | ......... A61K 31/7105 |
| WO | 2017/021546 A1 | 2/2017 | |
| WO | 2017/048770 A1 | 3/2017 | |
| WO | 2017/049245 A2 | 3/2017 | |
| WO | 2017/075531 A1 | 5/2017 | |
| WO | 2017/112865 A1 | 6/2017 | |
| WO | WO-2017112865 A1 * | 6/2017 | ......... A61K 38/1808 |
| WO | 2017/117528 A1 | 7/2017 | |
| WO | 2017/140905 A1 | 8/2017 | |
| WO | 2017/173054 A1 | 10/2017 | |
| WO | 2017/182634 A1 | 10/2017 | |
| WO | 2017/194454 A1 | 11/2017 | |
| WO | 2017/201332 A1 | 11/2017 | |
| WO | 2016/176330 A1 | 3/2018 | |
| WO | 2018/078053 A1 | 5/2018 | |
| WO | 2018/081480 A1 | 5/2018 | |
| WO | 2018/081638 A1 | 5/2018 | |
| WO | 2018/191657 A1 | 10/2018 | |
| WO | 2018/191719 A1 | 10/2018 | |
| WO | 2018/200943 A1 | 11/2018 | |
| WO | 2019/089828 A1 | 5/2019 | |
| WO | 2021/030701 A1 | 2/2021 | |

OTHER PUBLICATIONS

U.S. Appl. No. 17/317,517, filed May 11, 2021.
U.S. Appl. No. 17/371,261, filed Jul. 9, 2021.
U.S. Appl. No. 17/378,083, filed Jul. 16, 2021.
U.S. Appl. No. 17/496,530, filed Oct. 7, 2021.
U.S. Appl. No. 17/277,691, filed Mar. 18, 2021.
Akinc et al., "A combinatorial library of lipid-like materials for delivery of RNAi therapeutics," Nature Biotechnology 26(5):561-569, May 2008.
Akinc et al., "Targeted delivery of RNAi therapeutics with endogenous and exogenous ligand-based mechanisms," *Mol. Ther.* 18(7): 1357-1364, 2010.
Alabi et al., "Multiparametric approach for the evaluation of lipid nanoparticles for siRNA delivery," PNAS 110(32):12881-12886, Aug. 6, 2013.
Alexidis et al., "Novel 1,4 Substituted Piperidine Derivatives. Synthesis and Correlation of Antioxidant Activity with Structure and Lipophilicity," J. Pharm. Pharmacol. 47:131-137, 1995.
Anderson et al., "Incorporation of pseudouridine into mRNA enhances translation by diminishing PKR activation," *Nucleic Acids Res.* 38(17):5884-5892, 2010.
Anderson et al., "Nucleoside modifications in RNA limit activation of 2'-5'-oligoadenylate synthetase and increase resistance to cleavage by RNase L.," *Nucleic Acids Research* 39(21):9329-9338, 2011.
Ansell et al., "Application of Oligo-(14-amino-3,6,9,12-tetraoxatetradecanoic acid) Lipid Conjugates as Steric Barrier Molecules in Liposomal Formulations," *Bioconjugate Chem.* 10:653-666, 1999.
Ansell et al., "Novel Lipids and Lipid Nanoparticle Formulations for Delivery of Nucleic Acids," U.S. Appl. No. 17/317,517, filed May 11, 2021.
Argast et al., "I-PPOL and I-CREL Homing Site Sequence Degeneracy Determined by Random Mutagensis and Sequential in vitro Enrichment," *J. Mol. Biol.* 280:345-353, 1998.
Ashworth et al., "Computational Redesign of Endonuclease DNA Binding and Cleavage Specificity," *Nature* 441:656-659, 2006.
Basha et al., "Influence of cationic lipid composition on gene silencing properties of lipid nanoparticle formulations of siRNA in antigen-presenting cells," *Mol. Ther.* 19(12):2186-2200, 2011.
Beerli et al., "Engineering Polydactyl Zinc-Finger Transcription Factors," *Nature Biotechnology* 20:135-141, 2002.
Belfort et al., "Homing Endonucleases: Keeping the House in Order," *Nucleic Acids Research* 25:3379-3388, 1997.
Belliveau et al., "Microfluidic Synthesis of Highly Potent Limit-size Lipid Nanoparticles for In Vivo Delivery of siRNA," *Mol. Ther. Nucleic Acids* 1:e37, 2012 (9 pages).

(56) References Cited

OTHER PUBLICATIONS

Bhattacharya et al., "Synthesis, Thermotropic Behavior, and Permeability Properties of Vesicular Membranes Composed of Cationic Mixed-Chain Surfactants," *Langmuir* 11:4748-4757, 1995.
Boch et al., "Breaking the Code of DNA Binding Specificity of TAL-Type III Effectors," *Science* 326:1509-1512, 2009.
Boissel et al., "MegaTALs: A Rare-Cleaving Nuclease Architecture for Therapeutic Genome Engineering," *Nucl Acid Res* 42(4):42(4):2591-2601, 2014.
Bonas et al., "Genetic and Structural Characterization of the Avirulence Gene avrBS3 from *Xanthomonas campestris* PV, vesicatoria," *Mol Gen Genet* 218:127-136, 1989.
Brito et al., "A Cationic Nanoemulsion for the Delivery of Next-generation RNA Vaccines," *Molecular Therapy* 22(12):2118-2129, 2014.
Cattanach et al., "Studies in the Indole Series. Part IV. Tetrahydro-1H-pyrido[4,3-b]-indoles as Serotonin Antagonists," *J. Chem Soc. (C)*:1235-1243, 1968.
Chen et al., "Influence of particle size on the in vivo potency of lipid nanoparticle formulations of siRNA," *Journal of Controlled Release* 235:236-244, 2016.
Chen et al., "Rapid Discovery of Potent siRNA-Containing Lipid Nanoparticles Enabled by Controlled Microfluidic Formulation," *J. Am. Chem. Soc.* 134:6948-6951, 2012.
Chevalier et al., "Design, Activity, and Structure of a Highly Specific Artificial Endonuclease," *Molecular Cell* 10:895-905, 2002.
Choo et al., "Advances in Zinc Finger Engineering," *Current Opinion in Structural Biology* 10:411-416, 2000.
Cook et al., "Synthesis and Characterization of cis-Dioxomolybdenum(VI) Complexes with Sterically Bulky Tripodal Tetradentate Ligands," *Inorganica Chimica Acta* 144:81-87, 1988.
Dujon et al., "Mobile introns: definition of terms and recommend nomenclature," *Gene* 82:115-118, 1989.
Durbin et al., "RNAs Containing Modified Nucleotides Fail to Trigger RIG-I Conformational Changes for Innate Immune Signaling," *mBio* 7(5):e00833-16, 2016 (11 pages).
Epinat et al., "A novel engineered meganuclease induces homologous recombination in yeast and mammalian cells," *Nucleic Acids Research* 31:2952-2962, 2003.
Ernsting et al., "Factors controlling the pharmacokinetics, biodistribution and intratumoral penetration of nanoparticles," *Journal of Controlled Release* 172:782-794, 2013.
Fagerlund et al., "The Cpf1 CRISPR-Cas Protein Expands Genome-Editing Tools," *Genom Bio* 16:251, 2015 (3 pages).
Frisch et al. "A New Triantennary Galactose-Targeted PEGylated Gene Carrier, Characterization of Its Complex with DNA, and Transfection of Hepatoma Cells," *Bioconjugate Chem.* 15: 754-764, 2004.
Gimble et al., "Substrate Recognition and Induced DNA Distortion by the PI-SceI Endonuclease, an Enzyme Generated By Protein Splicing," *J. Mol. Biol.* 263:163-180, 1996.
Gronquist et al., "Synthesis of Unsaturated Polyazamacrolides from the Ladybird Beetle *Subcoccinella vigintiquatuorpunctata*," *J. Org. Chem.* 66:1075-1081, 2001.
Guilinger et al., "Fusion of Catalytically Inactive Cas9 to FoII Nuclease Improves the Specificity of Genome Modification," *Nature Biotech* 32(6):577-582, 2014.
Guo et al., "Directed Evolution of an Enhanced and Highly Efficient FokI Cleavage Domain for Zinc Finger Nucleases," *J. Mol. Biol.* 400(1):96-107, 2010.
Haft et al., "A Guild of 45 CRISPR-Associated (Cas) Protein Families and Multiple CRISPR/Cas Subtypes Exist in Prokaryotic Genomes," *PLoS Computational Biology* 1(6):e60, 2005.
Han et al., "Synthesis and Properties of Di-Chain Esterquat Surfactants," *J. Surfact Deterg.* 18: 91-95, 2015.
Hancock et al., "Monoalkylaminopropanols and Butanols and their Esters," *J. Am. Chem. Soc.* 66(10):1738-1747, 1944.
Hekele et al., "Rapidly produced SAM® vaccine against H7N9 influenza is immunogenic in mice," *Emerging Microbes and Infections* 2:e52, 2013 (7 pages).
Heuer et al., "Repeat Domain Diversity of avrBs3-Like Genes in *Ralstonia solancearum* Strains and Association with Host Preferences in the Field," *Applied and Environmental Microbiology* 73(13):4379-4384, 2007.
Isalan et al., "A rapid, generally applicable method to engineer zinc fingers illustrated by targeting the HIV-1 promoter," *Nat. Biotechnol* 19(7):656-660, 2001.
Jansen et al., "Identification of Genes that are Associated with DNA Repeats in Prokaryotes," *Molecular Microbiology* 43(6):1565-1575, 2002.
Jasin, "Genetic Manipulation of Genomes with Rare-Cutting Endonucleases," *Trends Genet* 12:224-228, 1996.
Jayaraman et al., "Maximizing the Potency of siRNA Lipid Nanoparticles for Hepatic Gene Silencing In Vivo," *Angew. Chem. Int. Ed.* 51(34):8529-8533, XP055063645, 2012.
Karikó et al., "Generating the optimal mRNA for therapy: HPLC purification eliminates immune activation and improves translation of nucleoside-modified, protein-encoding mRNA," *Nucleic Acids Research* 39(21):e142, 2011.
Karikó et al., "Incorporation of Pseudouridine into mRNA Yields Superior Nonimmunogenic Vector With Increased Translational Capacity and Biological Stability," *Mol. Ther.* 16(11):1833-1840, 2008.
Karikó et al., "Increased Erythropoiesis in Mice Injected with Submicrogram Quantities of Pseudouridine-containing mRNA Encoding Erythropoietin," *Mol. Ther.* 20(5):948-953, 2012.
Karikó et al., "Suppression of RNA Recognition by Toll-like Receptors: The Impact of Nucleoside Modification and the Evolutionary Origin of RNA," *Immunity* 23:165-175, 2005.
Kay et al., "A Bacterial Effector Acts as a Plant Transcription Factor and Induces a Cell Size Regulator," *Science* 318:648-651, 2007.
Kim et al., "Hybrid restriction enzymes: zinc finger fusions to Fok I cleavage domain," *PNAS USA* 93(3):1156-1160, 1996.
Kim et al., "Highly Efficient RNA-Guided Genome Editing in Human Cells via Delivery of Purified Cas9 Ribonucleoproteins," *Genome Research* 24(6):1012-1019, 2014.
Kormann et al., "Expression of therapeutic proteins after delivery of chemically modified mRNA in mice," *Nature Biotechnology* 29(2):154-157, 2011.
Lee et al., "Lipid nanoparticle siRNA systems for silencing the androgen receptor in human prostate cancer in vivo," *Int. J. Cancer* 131(5):E781-E790, 2012.
Leroueil et al., "Wide Varieties of Cationic Nanoparticles Induce Defects in Supported Lipid Bilayers," *Nano Letters* 8(2):420-424, 2008.
Leung et al., "Lipid Nanoparticles Containing siRNA Synthesized by Microfluidic Mixing Exhibit an Electron-Dense Nanostructured Core," *J. Phys. Chem. C. Nanomater. Interfaces* 116(34):18440-18450, 2012.
Leung et al., "Microfluidic Mixing: A General Method for Encapsulating Macromolecules in Lipid Nanoparticle Systems," *J. Phys. Chem. B* 119:8698-8706, 2015.
Li et al., "ATRP in Waterborne Miniemulsion via a Simultaneous Reverse and Normal Initiation Process," *Macromolecules* 37(6):2106-2112, 2004.
Mahon et al., "A combinatorial approach to determine functional group effects on lipidoid-mediated siRNA delivery," *Bioconjug Chem.* 21(8):1448-1454, 2010. (17 pages).
Maier et al., "Biodegradable lipids enabling rapidly eliminated lipid nanoparticles for systemic delivery of RNAi therapeutics," *Mol. Ther.* 21(8):1570-1578, 2013.
Makarova et al., "A DNA Repair System Specific for Thermophilic Archaea and Bacteria Predicted by Genomic Context Analysis," *Nucleic Acids Research* 30(2):482-496, 2002.
Makarova et al., "A Putative RNA-Interference-Based Immune System in Prokaryotes: Computational Analysis of the Predicted Enzymatic Machinery, Functional Analogies with Eukaryotic RNAi, and Hypothetical Mechanisms of Action," *Biology Direct* 1:7, 2006.
Marchi-Artzner et al., "Adhesion of Arg-Gly-Asp (RGD) Peptide Vesicles onto an Integrin Surface: Visualization of the Segregation of RGD Ligands into the Adhesion Plaques by Fluorescence," *Langmuir* 19:835-841, 2003.

(56) References Cited

OTHER PUBLICATIONS

Masuda et al., "Envelope-type lipid nanoparticles incorporating a short PEG-lipid conjugate for improved control of intracellular trafficking and transgene transcription," *Biomaterials 30*:4806-4814, 2009.

McCaffrey et al., "CRISPR-CAS9 D10A Nickase Target-Specific Fluorescent Labeling of Double Stand DNA for Whole Genome Mapping and Structural Variation Analysis," *Nucleic Acids Res 44*(2):e11.doi: 10.1093/ar/gkv878, 2015.

Miller et al., "An improved zinc-finger nuclease architecture for highly specific genome editing," *Nat. Biotechnology 25*:778-785, 2007.

Moscou et al., "A Simple Cipher Governs Data Recognition by TAL Effectors," *Science 326*:1501, 2009 (2 pages).

Mui et al., "Influence of Polyethylene Glycol Lipid Desorption Rates on Pharmacokinetics and Pharmacodynamics of siRNA Lipid Nanoparticles," *Mol. Ther. Nucleic Acids 2*:e139, 2013 (8 pages).

Nguyen et al., "Lipid-derived nanoparticles for immunostimulatory RNA adjuvant delivery", Proceedings of the National Academy of Sciences 109(14):E797-E803, 2012.

Nishida, "Disk-shaped magnetic recording medium," CAPLUS Database, Accession No. 2001:881906, 2001 (1 page).

Olovnikov et al., "Bacterial Argonaute samples the transcriptome to identify foreign DNA," *Mol. Cell. 51*(5):594-605, 2013.

Pabo et al., "Design and Selection of Novel $Cys_2$-$His_2$ Zinc Finger Proteins," *Ann. Rev. Biochem. 70*:313-340, 2001.

Pâques et al., "Meganucleases and DNA Double-Strand Break-Induced Recombination: Perspectives for Gene Therapy," *Current Gene Therapy 7*:49-66, 2007.

Pardi et al., "Expression kinetics of nucleoside-modified mRNA delivered in lipid nanoparticles to mice by various routes," *Journal of Controlled Release 217*:345-351, 2015.

Petsch et al., "Protective efficacy of in vitro synthesized, specific mRNA vaccines against influenza A virus infection," *Nature Biotechnology 30*(12):1210-1216, 2012 (9 pages).

Perez et al., "Establishment of HIV-1 Resistance in $CD4^+$ T Cells by Genome Editing Using Zinc-Finger Nucleases," *Nature Biotechnology 26*(7):808-816, 2008.

Perler et al., "Protein splicing elements: inteins and exteins a definition of terms and recommended nomenclature," *Nucleic Acids Research 22*:1125-1127, 1994.

Rajesh et al., "Dramatic Influence of the Orientation of Linker between Hydrophilic and Hydrophobic Lipid Moiety in Liposomal Gene Delivery," *Journal of the American Chemical Society 129*(37):11408-11420, 2007.

Ran et al., "In Vivo Genome Editing Using *Staphylococcus aureus* Cas9," *Nature 520*:186-194, 2015.

Russell et al., "The Stability of Human β-Globin mRNA is Dependent on Structural Determinants Positioned Within Its 3' Untranslated Region," *Blood 87*:5314-5323, 1996.

Schar et al., "Long Chain Linear Fatty Alcohols from ZIEGLER-Synthesis, their Mixtures, Derivatives and Use," IP.com Prior Art Database Technical Disclosure, Jan. 17, 2011, 39 pages.

Schnee et al., "An mRNA Vaccine Encoding Rabies Virus Glycoprotein Induces Protection against Lethal Infection in Mice and Correlates of Protection in Adult and Newborn Pigs," *PLoS Negl. Trop. Dis. 10*(6):e0004746, 2016 (20 pages).

Schornack et al., "Gene-for-Gene-Mediated Recognition of Nuclear-Targeted AvrBs3-Like Bacterial Effector Proteins," *Journal of Plant Physiology 163*(3):256-272, 2006.

Segal et al., "Custom DNA-binding proteins come of age: polydactyl zinc-finger proteins," *Current Opinion Biotechnology 12*:632-637, 2001.

Semple et al., "Interactions of liposomes and lipid-based carrier systems with blood proteins: Relation to clearance behaviour in vivo," Advanced Drug Delivery Reviews 32:3-17, 1998.

Semple et al., "Rational design of cationic lipids for siRNA delivery," *Nature Biotechnology 28*(2):172-176, 2010. (26 pages).

Sheng et al., "Structure-Based cleavage mechanism of *Thermus thermophilus* argonaute dna guide strand-mediated dna target cleavage," *Proc. Natl. Acad. Sci. USA 111*(2):652-657, 2014.

Smietanski et al., "Structural analysis of human 2'-O-ribose methyltransferases involved in mRNA cap structure formation," *Nature Communications 5*:3004, 2014.

Swarts et al., "DNA-Guided DNA Interference by a Prokaryotic Argonaute," *Nature 507*(7491):258-261, 2014.

Szebeni et al., "Activation of complement by therapeutic liposomes and other lipid excipient-based therapeutic products: Prediction and prevention," *Advanced Drug Delivery Reviews 63*:1020-1030, 2011.

Szebeni et al., "Complement activation as a bioequivalence issue relevant to the development of generic liposomes and other nanoparticulate drugs," *Biochemical and Biophysical Research Communications 468*:490-497, 2015.

Szebeni, "Complement activation-related pseudoallergy: A stress reaction in blood triggered by nanomedicines and biologicals," *Molecular Immunology 61*:163-173, 2014.

Szolcsányi et al., "Short racemic syntheses of calvine and epicalvine," *Tetrahedron Letters 49*:1357-1360, 2008.

Tam et al., "Advances in Lipid Nanoparticles for siRNA Delivery," *Pharmaceutics 5*:498-507, 2013.

Tam et al., "Small molecule ligands for enhanced intracellular delivery of lipid nanoparticle formulations of siRNA," *Nanomedicine 9*(5):665-674, 2013.

Tekmira Pharmaceuticals Corp, Form 20-F, EDGAR Online, filed Mar. 27, 2013, 298 pages.

Tekmira, "Tekmira and Alnylam Restructure Relationship and Settle All Litigation," Tekmira Pharmaceuticals Corporation, Nov. 12, 2012, 3 pages.

Torrecilla et al., "Lipid Nanoparticles as Carriers for RNAi against Viral Infections: Current Status and Future Perspectives," BioMed Research International 2014:Article ID 161794, 17 pages.

Urnov et al., "Highly Efficient Endogenous Human Gene Correction Using Designed Zinc-Finger Nucleases," *Nature 435*(7042):646-651, 2005.

Van Doren et al., "Structure-Property Relationships in D-Glucitol Derivatives with Two Geminal Hydrocarbon Chains," *J. Mater. Chem. 5*(12):2153-2160, 1995.

Vogel et al., "A Bacterial Seek-and-Destroy System for Foreign DNA," *Science 344*(6187):972-73, 2014.

Wang et al., "Composite Nanoparticles for Gene Delivery," *Adv. Genet. 88*:111-137, 2014.

Whitehead et al., "Synergistic Silencing: Combinations of Lipid-like Materials for Efficacious siRNA Delivery," *Molecular Therapy 19*(9):1688-1694, 2011.

Wilson et al., "The Combination of Stabilized Plasmid Lipid Particles and Lipid Nanoparticle Encapsulated CpG Containing Oligodeoxynucleotides as Systemic Genetic Vaccine," *The Journal of Gene Medicine 11*(1):14-25, 2009.

Xue et al., "Lipid-Based Nanocarriers for RNA Delivery," *Current Pharmaceutical Design 21*:3140-3147, 2015.

Yin et al., "Therapeutic Genome Editing By Combined Viral and Non-Viral Delivery of CRISPR System Components in vivo," *Nat. Biotech 34*(3):328, 2016.

Yoshimura et al., "Solution Properties of Tadpole-type Cationic Amphiphilic Dendrimers Consisting of an Alkyl Chain, a Quaternary Ammonium, and a Poly(amidoamine) Dendron," Journal of Oleo Science 62(4):213-221, 2013.

Yuan et al., "Crystal Structure of *A. aeolicus* Argonaute, A Site-Specific DNA-Guided Endoribonuclease, Provides Insights Into RISC-Mediated mRNA Cleavage," *Molecular Cell 19*:405-419, 2005.

Zanta-Boussif et al., "Validation of a mutated PRE sequence allowing high and sustained transgene expression while abrogating WHV-X protein synthesis: application to the gene therapy of WAS," *Gene Therapy 16*:605-619, 2009.

Zhang et al., "Biodegradable Amino-Ester Nanomaterials for Cas9 mRNA Delivery in Vitro and in Vivo," *ACS Appl. Mater. Interfaces 9*(30):25481-25487, 2017. (15 pages).

Zhang et al., "Lipid-modified spermine derivatives and liposome prepared with said derivatives," CAPLUS Database, Accession No. 2015:1437089, 2015. (2 pages).

(56) References Cited

OTHER PUBLICATIONS

U.S. Appl. No. 17/634,516, filed Feb. 10, 2022.
Chaves et al., "A novel tripodal tris-hydroxypyrimidinone sequestering agent for trivalent hard metal ions: synthesis, complexation and in vivo studies," Dalton Transactions 42(17):6033-6045, 2013.
Higashi et al., "Novel lipidated sorbitol-based molecular transporters for non-viral gene delivery," Journal of Controlled Release 136:140-147, 2009.
Kim et al., "Synthesis of Novel Poly(amido ethylenimine) (PAMEIM) Dendrimer and Its Self-assembly with Plasmid DNA," Bull. Korean Chem. Soc. 27(11):1894-1896, 2006.
Leriche et al., "Investigation of Dendriplexes by Ion Mobility-Mass Spectrometry," Molecules 19(12):20731-20750, Dec. 12, 2014.
Mendonça et al., "New tris-3,4-HOPO lanthanide complexes as potential imaging probes: complex stability and magnetic properties," Dalton Transactions 42(17):6046-6057, 2013.
Patani et al., "Bioisosterism: A Rational Approach in Drug Design," Chem. Rev. 96(8):3147-3176, 1996.
Santo et al., "Hydrogen bonding interactions between Starburst dendrimers and several molecules of biological interest," J Phys Org Chem 12(4):293-307, Apr. 1999.

\* cited by examiner

LIPIDS FOR USE IN LIPID NANOPARTICLE FORMULATIONS

BACKGROUND

Technical Field

Embodiments of the present invention generally relate to novel lipids that can be used in combination with other lipid components, such as neutral lipids, cholesterol and polymer conjugated lipids, to form lipid nanoparticles for delivery of therapeutic agents, such as nucleic acids (e.g., oligonucleotides, messenger RNA), both in vitro and in vivo.

Description of the Related Art

There are many challenges associated with the delivery of nucleic acids to affect a desired response in a biological system. Nucleic acid based therapeutics have enormous potential but there remains a need for more effective delivery of nucleic acids to appropriate sites within a cell or organism in order to realize this potential. Therapeutic nucleic acids include, e.g., messenger RNA (mRNA), antisense oligonucleotides, ribozymes, DNAzymes, plasmids, immune stimulating nucleic acids, antagomir, antimir, mimic, supermir, and aptamers. Some nucleic acids, such as mRNA or plasmids, can be used to effect expression of specific cellular products as would be useful in the treatment of, for example, diseases related to a deficiency of a protein or enzyme. The therapeutic applications of translatable nucleotide delivery are extremely broad as constructs can be synthesized to produce any chosen protein sequence, whether or not indigenous to the system. The expression products of the nucleic acid can augment existing levels of protein, replace missing or non-functional versions of a protein, or introduce new protein and associated functionality in a cell or organism.

Some nucleic acids, such as miRNA inhibitors, can be used to effect expression of specific cellular products that are regulated by miRNA as would be useful in the treatment of, for example, diseases related to deficiency of protein or enzyme. The therapeutic applications of miRNA inhibition are extremely broad as constructs can be synthesized to inhibit one or more miRNA that would in turn regulate the expression of mRNA products. The inhibition of endogenous miRNA can augment its downstream target endogenous protein expression and restore proper function in a cell or organism as a means to treat disease associated to a specific miRNA or a group of miRNA.

Other nucleic acids can down-regulate intracellular levels of specific mRNA and, as a result, down-regulate the synthesis of the corresponding proteins through processes such as RNA interference (RNAi) or complementary binding of antisense RNA. The therapeutic applications of antisense oligonucleotide and RNAi are also extremely broad, since oligonucleotide constructs can be synthesized with any nucleotide sequence directed against a target mRNA. Targets may include mRNAs from normal cells, mRNAs associated with disease-states, such as cancer, and mRNAs of infectious agents, such as viruses. To date, antisense oligonucleotide constructs have shown the ability to specifically down-regulate target proteins through degradation of the cognate mRNA in both in vitro and in vivo models. In addition, antisense oligonucleotide constructs are currently being evaluated in clinical studies.

However, two problems currently face the use of oligonucleotides in therapeutic contexts. First, free RNAs are susceptible to nuclease digestion in plasma. Second, free RNAs have limited ability to gain access to the intracellular compartment where the relevant translation machinery resides. Lipid nanoparticles formed from lipids formulated with other lipid components, such as neutral lipids, cholesterol, PEG, PEGylated lipids, and oligonucleotides have been used to block degradation of the RNAs in plasma and facilitate the cellular uptake of the oligonucleotides.

There remains a need for improved lipids and lipid nanoparticles for the delivery of oligonucleotides. Preferably, these lipid nanoparticles would provide optimal drug: lipid ratios, protect the nucleic acid from degradation and clearance in serum, be suitable for systemic or local delivery, and provide intracellular delivery of the nucleic acid. In addition, these lipid-nucleic acid particles should be well-tolerated and provide an adequate therapeutic index, such that patient treatment at an effective dose of the nucleic acid is not associated with unacceptable toxicity and/or risk to the patient. The present invention provides these and related advantages.

BRIEF SUMMARY

In brief, embodiments of the present invention provide lipid compounds, including stereoisomers, pharmaceutically acceptable salts, prodrugs or tautomers thereof, which can be used alone or in combination with other lipid components such as neutral lipids, charged lipids, steroids (including for example, all sterols) and/or their analogs, and/or polymer conjugated lipids to form lipid nanoparticles for the delivery of therapeutic agents. In some instances, the lipid nanoparticles are used to deliver nucleic acids such as antisense and/or messenger RNA. Methods for use of such lipid nanoparticles for treatment of various diseases or conditions, such as those caused by infectious entities and/or insufficiency of a protein, are also provided.

In one embodiment, compounds having the following structure (I) are provided:

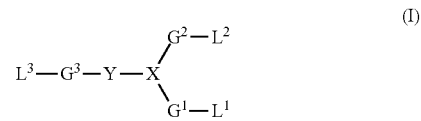

(I)

or a pharmaceutically acceptable salt, tautomer, prodrug or stereoisomer thereof, wherein X, Y, $L^1$, $L^2$, $L^3$, $G^1$, $G^2$ and $G^3$ are as defined herein.

Pharmaceutical compositions comprising one or more of the foregoing compounds of structure (I) and a therapeutic agent are also provided. Also provided are lipid nanoparticles (LNPs) comprising one or more compounds of structure (I). In some embodiments, the pharmaceutical compositions and/or LNPs further comprise one or more components selected from neutral lipids, charged lipids, steroids and polymer conjugated lipids. The disclosed compositions are useful for formation of lipid nanoparticles for the delivery of the therapeutic agent.

In other embodiments, the present invention provides a method for administering a therapeutic agent to a patient in need thereof, the method comprising preparing a composition of lipid nanoparticles comprising the compound of structure (I) and a therapeutic agent and delivering the composition to the patient. In some embodiments the method for administering a therapeutic agent to a patient in

DETAILED DESCRIPTION need thereof comprises administering an LNP comprising one or more compounds of structure (I) and the therapeutic agent to the patient.

These and other aspects of the invention will be apparent upon reference to the following detailed description.

In the following description, certain specific details are set forth in order to provide a thorough understanding of various embodiments of the invention. However, one skilled in the art will understand that embodiments of the invention may be practiced without these details.

Embodiments of the present invention are based, in part, upon the discovery of novel lipids that provide advantages when used in lipid nanoparticles for the in vivo delivery of an active or therapeutic agent such as a nucleic acid into a cell of a mammal. In particular, embodiments the present invention provides nucleic acid-lipid nanoparticle compositions comprising one or more of the novel lipids described herein that provide increased activity of the nucleic acid and improved tolerability of the compositions in vivo, resulting in a significant increase in the therapeutic index as compared to nucleic acid-lipid nanoparticle compositions previously described. For example, embodiments provide a lipid nanoparticle comprising one or more compounds of structure (I).

In particular embodiments, the present invention provides novel lipids that enable the formulation of improved compositions for the in vitro and in vivo delivery of mRNA and/or other oligonucleotides. In some embodiments, these improved lipid nanoparticle compositions are useful for expression of protein encoded by mRNA. In other embodiments, these improved lipid nanoparticles compositions are useful for upregulation of endogenous protein expression by delivering miRNA inhibitors targeting one specific miRNA or a group of miRNA regulating one target mRNA or several mRNA. In other embodiments, these improved lipid nanoparticle compositions are useful for down-regulating (e.g., silencing) the protein levels and/or mRNA levels of target genes. In some other embodiments, the lipid nanoparticles are also useful for delivery of mRNA and plasmids for expression of transgenes. In yet other embodiments, the lipid nanoparticle compositions are useful for inducing a pharmacological effect resulting from expression of a protein, e.g., increased production of red blood cells through the delivery of a suitable erythropoietin mRNA, or protection against infection through delivery of mRNA encoding for a suitable antigen or antibody.

The lipid nanoparticles and compositions of embodiments of the present invention may be used for a variety of purposes, including the delivery of encapsulated or associated (e.g., complexed) therapeutic agents such as nucleic acids to cells, both in vitro and in vivo. Accordingly, embodiments of the present invention provide methods of treating or preventing diseases or disorders in a subject in need thereof by contacting the subject with a lipid nanoparticle that encapsulates or is associated with a suitable therapeutic agent, wherein the lipid nanoparticle comprises one or more of the novel lipids described herein.

As described herein, embodiments of the lipid nanoparticles of the present invention are particularly useful for the delivery of nucleic acids, including, e.g., mRNA, antisense oligonucleotide, plasmid DNA, microRNA (miRNA), miRNA inhibitors (antagomirs/antimirs), messenger-RNA-interfering complementary RNA (micRNA), DNA, multivalent RNA, dicer substrate RNA, complementary DNA (cDNA), etc. Therefore, the lipid nanoparticles and compositions of embodiments of the present invention may be used to induce expression of a desired protein both in vitro and in vivo by contacting cells with a lipid nanoparticle comprising one or more novel lipids described herein, wherein the lipid nanoparticle encapsulates or is associated with a nucleic acid that is expressed to produce the desired protein (e.g., a messenger RNA or plasmid encoding the desired protein) or inhibit processes that terminate expression of mRNA (e.g., miRNA inhibitors). Alternatively, the lipid nanoparticles and compositions of embodiments of the present invention may be used to decrease the expression of target genes and proteins both in vitro and in vivo by contacting cells with a lipid nanoparticle comprising one or more novel lipids (e.g., a compound of structure (I)) described herein, wherein the lipid nanoparticle encapsulates or is associated with a nucleic acid that reduces target gene expression (e.g., an antisense oligonucleotide or small interfering RNA (siRNA)). The lipid nanoparticles and compositions of embodiments of the present invention may also be used for co-delivery of different nucleic acids (e.g., mRNA and plasmid DNA) separately or in combination, such as may be useful to provide an effect requiring colocalization of different nucleic acids (e.g., mRNA encoding for a suitable gene modifying enzyme and DNA segment(s) for incorporation into the host genome).

Nucleic acids for use with embodiments of this invention may be prepared according to any available technique. For mRNA, the primary methodology of preparation is, but not limited to, enzymatic synthesis (also termed in vitro transcription) which currently represents the most efficient method to produce long sequence-specific mRNA. In vitro transcription describes a process of template-directed synthesis of RNA molecules from an engineered DNA template comprised of an upstream bacteriophage promoter sequence (e.g., including but not limited to that from the T7, T3 and SP6 coliphage) linked to a downstream sequence encoding the gene of interest. Template DNA can be prepared for in vitro transcription from a number of sources with appropriate techniques which are well known in the art including, but not limited to, plasmid DNA and polymerase chain reaction amplification (see Linpinsel, J. L and Conn, G. L., General protocols for preparation of plasmid DNA template and Bowman, J. C., Azizi, B., Lenz, T. K., Ray, P., and Williams, L. D. in RNA in vitro transcription and RNA purification by denaturing PAGE in Recombinant and in vitro RNA syntheses Methods v. 941 Conn G. L. (ed), New York, N.Y. Humana Press, 2012)

Transcription of the RNA occurs in vitro using the linearized DNA template in the presence of the corresponding RNA polymerase and adenosine, guanosine, uridine and cytidine ribonucleoside triphosphates (rNTPs) under conditions that support polymerase activity while minimizing potential degradation of the resultant mRNA transcripts. In vitro transcription can be performed using a variety of commercially available kits including, but not limited to RiboMax Large Scale RNA Production System (Promega), MegaScript Transcription kits (Life Technologies) as well as with commercially available reagents including RNA polymerases and rNTPs. The methodology for in vitro transcription of mRNA is well known in the art. (see, e.g., Losick, R., 1972, In vitro transcription, Ann Rev Biochem v. 41 409-46; Kamakaka, R. T. and Kraus, W. L. 2001. In Vitro Transcription. Current Protocols in Cell Biology. 2:11.6:11.6.1-11.6.17; Beckert, B. And Masquida, B., (2010) Synthesis of RNA by In Vitro Transcription in RNA in Methods in Molecular Biology v. 703 (Neilson, H. Ed), New York, N.Y.

Humana Press, 2010; Brunelle, J. L. and Green, R., 2013, Chapter Five—In vitro transcription from plasmid or PCR-amplified DNA, Methods in Enzymology v. 530, 101-114; all of which are incorporated herein by reference).

The desired in vitro transcribed mRNA is then purified from the undesired components of the transcription or associated reactions (including unincorporated rNTPs, protein enzyme, salts, short RNA oligos, etc.). Techniques for the isolation of the mRNA transcripts are well known in the art. Well known procedures include phenol/chloroform extraction or precipitation with either alcohol (ethanol, isopropanol) in the presence of monovalent cations or lithium chloride. Additional, non-limiting examples of purification procedures which can be used include size exclusion chromatography (Lukavsky, P. J. and Puglisi, J. D., 2004, Large-scale preparation and purification of polyacrylamide-free RNA oligonucleotides, RNA v. 10, 889-893), silica-based affinity chromatography and polyacrylamide gel electrophoresis (Bowman, J. C., Azizi, B., Lenz, T. K., Ray, P., and Williams, L. D. in RNA in vitro transcription and RNA purification by denaturing PAGE in Recombinant and in vitro RNA syntheses Methods v. 941 Conn G. L. (ed), New York, N.Y. Humana Press, 2012). Purification can be performed using a variety of commercially available kits including, but not limited to SV Total Isolation System (Promega) and In Vitro Transcription Cleanup and Concentration Kit (Norgen Biotek).

Furthermore, while reverse transcription can yield large quantities of mRNA, the products can contain a number of aberrant RNA impurities associated with undesired polymerase activity which may need to be removed from the full-length mRNA preparation. These include short RNAs that result from abortive transcription initiation as well as double-stranded RNA (dsRNA) generated by RNA-dependent RNA polymerase activity, RNA-primed transcription from RNA templates and self-complementary 3' extension. It has been demonstrated that these contaminants with dsRNA structures can lead to undesired immunostimulatory activity through interaction with various innate immune sensors in eukaryotic cells that function to recognize specific nucleic acid structures and induce potent immune responses. This in turn, can dramatically reduce mRNA translation since protein synthesis is reduced during the innate cellular immune response. Therefore, additional techniques to remove these dsRNA contaminants have been developed and are known in the art including but not limited to scaleable HPLC purification (see, e.g., Kariko, K., Muramatsu, H., Ludwig, J. And Weissman, D., 2011, Generating the optimal mRNA for therapy: HPLC purification eliminates immune activation and improves translation of nucleoside-modified, protein-encoding mRNA, Nucl Acid Res, v. 39 e142; Weissman, D., Pardi, N., Muramatsu, H., and Kariko, K., HPLC Purification of in vitro transcribed long RNA in Synthetic Messenger RNA and Cell Metabolism Modulation in Methods in Molecular Biology v. 969 (Rabinovich, P. H. Ed), 2013). HPLC purified mRNA has been reported to be translated at much greater levels, particularly in primary cells and in vivo.

A significant variety of modifications have been described in the art which are used to alter specific properties of in vitro transcribed mRNA, and improve its utility. These include, but are not limited to modifications to the 5' and 3' termini of the mRNA. Endogenous eukaryotic mRNA typically contain a cap structure on the 5'-end of a mature molecule which plays an important role in mediating binding of the mRNA Cap Binding Protein (CBP), which is in turn responsible for enhancing mRNA stability in the cell and efficiency of mRNA translation. Therefore, highest levels of protein expression are achieved with capped mRNA transcripts. The 5'-cap contains a 5'-5'-triphosphate linkage between the 5'-most nucleotide and guanine nucleotide. The conjugated guanine nucleotide is methylated at the N7 position. Additional modifications include methylation of the ultimate and penultimate most 5'-nucleotides on the 2'-hydroxyl group.

Multiple distinct cap structures can be used to generate the 5'-cap of in vitro transcribed synthetic mRNA. 5'-capping of synthetic mRNA can be performed co-transcriptionally with chemical cap analogs (i.e. capping during in vitro transcription). For example, the Anti-Reverse Cap Analog (ARCA) cap contains a 5'-5'-triphosphate guanine-guanine linkage where one guanine contains an N7 methyl group as well as a 3'-O-methyl group. However, up to 20% of transcripts remain uncapped during this co-transcriptional process and the synthetic cap analog is not identical to the 5'-cap structure of an authentic cellular mRNA, potentially reducing translatability and cellular stability. Alternatively, synthetic mRNA molecules may also be enzymatically capped post-transcriptionally. These may generate a more authentic 5'-cap structure that more closely mimics, either structurally or functionally, the endogenous 5'-cap which have enhanced binding of cap binding proteins, increased half-life, reduced susceptibility to 5' endonucleases, and/or reduced 5' decapping. Numerous synthetic 5'-cap analogs have been developed and are known in the art to enhance mRNA stability and translatability (see, e.g., Grudzien-Nogalska, E., Kowalska, J., Su, W., Kuhn, A. N., Slepenkov, S. V., Darynkiewicz, E., Sahin, U., Jemielity, J., and Rhoads, R. E., Synthetic mRNAs with superior translation and stability properties in Synthetic Messenger RNA and Cell Metabolism Modulation in Methods in Molecular Biology v. 969 (Rabinovich, P. H. Ed), 2013).

On the 3'-terminus, a long chain of adenine nucleotides (poly-A tail) is normally added to mRNA molecules during RNA processing. Immediately after transcription, the 3' end of the transcript is cleaved to free a 3' hydroxyl to which poly-A polymerase adds a chain of adenine nucleotides to the RNA in a process called polyadenylation. The poly-A tail has been extensively shown to enhance both translational efficiency and stability of mRNA (see Bernstein, P. and Ross, J., 1989, Poly (A), poly (A) binding protein and the regulation of mRNA stability, Trends Bio Sci v. 14 373-377; Guhaniyogi, J. And Brewer, G., 2001, Regulation of mRNA stability in mammalian cells, Gene, v. 265, 11-23; Dreyfus, M. And Regnier, P., 2002, The poly (A) tail of mRNAs: Bodyguard in eukaryotes, scavenger in bacteria, Cell, v. 111, 611-613).

Poly (A) tailing of in vitro transcribed mRNA can be achieved using various approaches including, but not limited to, cloning of a poly (T) tract into the DNA template or by post-transcriptional addition using Poly (A) polymerase. The first case allows in vitro transcription of mRNA with poly (A) tails of defined length, depending on the size of the poly (T) tract, but requires additional manipulation of the template. The latter case involves the enzymatic addition of a poly (A) tail to in vitro transcribed mRNA using poly (A) polymerase which catalyzes the incorporation of adenine residues onto the 3'termini of RNA, requiring no additional manipulation of the DNA template, but results in mRNA with poly(A) tails of heterogeneous length. 5'-capping and 3'-poly (A) tailing can be performed using a variety of commercially available kits including, but not limited to Poly (A) Polymerase Tailing kit (Epicenter), mMESSAGE mMACHINE T7 Ultra kit and Poly (A) Tailing kit (Life Technologies) as well as with commercially available reagents, various ARCA caps, Poly (A) polymerase, etc.

In addition to 5' cap and 3' poly adenylation, other modifications of the in vitro transcripts have been reported to provide benefits as related to efficiency of translation and stability. It is well known in the art that pathogenic DNA and RNA can be recognized by a variety of sensors within eukaryotes and trigger potent innate immune responses. The ability to discriminate between pathogenic and self DNA and RNA has been shown to be based, at least in part, on structure and nucleoside modifications since most nucleic acids from natural sources contain modified nucleosides In contrast, in vitro synthesized RNA lacks these modifications, thus rendering it immunostimulatory which in turn can inhibit effective mRNA translation as outlined above. The introduction of modified nucleosides into in vitro transcribed mRNA can be used to prevent recognition and activation of RNA sensors, thus mitigating this undesired immunostimulatory activity and enhancing translation capacity (see e.g. Kariko, K. And Weissman, D. 2007, Naturally occurring nucleoside modifications suppress the immunostimulatory activity of RNA: implication for therapeutic RNA development, Curr Opin Drug Discov Devel, v. 10 523-532; Pardi, N., Muramatsu, H., Weissman, D., Kariko, K., In vitro transcription of long RNA containing modified nucleosides in Synthetic Messenger RNA and Cell Metabolism Modulation in Methods in Molecular Biology v. 969 (Rabinovich, P. H. Ed), 2013); Kariko, K., Muramatsu, H., Welsh, F. A., Ludwig, J., Kato, H., Akira, S., Weissman, D., 2008, Incorporation of Pseudouridine Into mRNA Yields Superior Nonimmunogenic Vector With Increased Translational Capacity and Biological Stability, Mol Ther v. 16, 1833-1840. The modified nucleosides and nucleotides used in the synthesis of modified RNAs can be prepared monitored and utilized using general methods and procedures known in the art. A large variety of nucleoside modifications are available that may be incorporated alone or in combination with other modified nucleosides to some extent into the in vitro transcribed mRNA (see e.g. US2012/0251618). In vitro synthesis of nucleoside-modified mRNA have been reported to have reduced ability to activate immune sensors with a concomitant enhanced translational capacity.

Other components of mRNA which can be modified to provide benefit in terms of translatability and stability include the 5' and 3' untranslated regions (UTR). Optimization of the UTRs (favorable 5' and 3' UTRs can be obtained from cellular or viral RNAs), either both or independently, have been shown to increase mRNA stability and translational efficiency of in vitro transcribed mRNA (see e.g. Pardi, N., Muramatsu, H., Weissman, D., Kariko, K., In vitro transcription of long RNA containing modified nucleosides in Synthetic Messenger RNA and Cell Metabolism Modulation in Methods in Molecular Biology v. 969 (Rabinovich, P. H. Ed), 2013).

In addition to mRNA, other nucleic acid payloads may be used for embodiments of this invention. For oligonucleotides, methods of preparation include but are not limited to chemical synthesis and enzymatic, chemical cleavage of a longer precursor, in vitro transcription as described above, etc. Methods of synthesizing DNA and RNA nucleotides are widely used and well known in the art (see, e.g. Gait, M. J. (ed.) Oligonucleotide synthesis: a practical approach, Oxford [Oxfordshire], Washington, D.C.: IRL Press, 1984; and Herdewijn, P. (ed.) Oligonucleotide synthesis: methods and applications, Methods in Molecular Biology, v. 288 (Clifton, N.J.) Totowa, N.J.: Humana Press, 2005; both of which are incorporated herein by reference).

For plasmid DNA, preparation for use with embodiments of this invention commonly utilizes but is not limited to expansion and isolation of the plasmid DNA in vitro in a liquid culture of bacteria containing the plasmid of interest. The presence of a gene in the plasmid of interest that encodes resistance to a particular antibiotic (penicillin, kanamycin, etc.) allows those bacteria containing the plasmid of interest to selectively grow in antibiotic-containing cultures. Methods of isolating plasmid DNA are widely used and well known in the art (see, e.g. Heilig, J., Elbing, K. L. and Brent, R (2001) Large-Scale Preparation of Plasmid DNA. Current Protocols in Molecular Biology. 41:11:1.7: 1.7.1-1.7.16; Rozkov, A., Larsson, B., Gillström, S., Björnestedt, R. and Schmidt, S. R. (2008), Large-scale production of endotoxin-free plasmids for transient expression in mammalian cell culture. Biotechnol. Bioeng., 99: 557-566; and U.S. Pat. No. 6,197,553B1). Plasmid isolation can be performed using a variety of commercially available kits including, but not limited to Plasmid Plus (Qiagen), GenJET plasmid MaxiPrep (Thermo) and PureYield MaxiPrep (Promega) kits as well as with commercially available reagents.

Various exemplary embodiments of the lipids of the present invention, lipid nanoparticles and compositions comprising the same, and their use to deliver active (e.g. therapeutic agents), such as nucleic acids, to modulate gene and protein expression, are described in further detail below.

As used herein, the following terms have the meanings ascribed to them unless specified otherwise.

Unless the context requires otherwise, throughout the present specification and claims, the word "comprise" and variations thereof, such as, "comprises" and "comprising" are to be construed in an open and inclusive sense, that is, as "including, but not limited to".

Reference throughout this specification to "one embodiment" or "an embodiment" means that a particular feature, structure or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

Unless defined otherwise, all technical and scientific terms used herein have the same meaning as is commonly understood by one of skill in the art to which this invention belongs. As used in the specification and claims, the singular form "a", "an" and "the" include plural references unless the context clearly dictates otherwise.

The phrase "induce expression of a desired protein" refers to the ability of a nucleic acid to increase expression of the desired protein. To examine the extent of protein expression, a test sample (e.g. a sample of cells in culture expressing the desired protein) or a test mammal (e.g. a mammal such as a human or an animal model such as a rodent (e.g. mouse) or a non-human primate (e.g., monkey) model) is contacted with a nucleic acid (e.g. nucleic acid in combination with a lipid of the present invention). Expression of the desired protein in the test sample or test animal is compared to expression of the desired protein in a control sample (e.g. a sample of cells in culture expressing the desired protein) or a control mammal (e.g., a mammal such as a human or an animal model such as a rodent (e.g. mouse) or non-human primate (e.g. monkey) model) that is not contacted with or administered the nucleic acid. When the desired protein is present in a control sample or a control mammal, the expression of a desired protein in a control sample or a control mammal may be assigned a value of 1.0. In particular embodiments, inducing expression of a desired protein is achieved when the ratio of desired protein expression in the test sample or the test mammal to the level of desired protein expression in the control sample or the control mammal is greater than 1, for example, about 1.1, 1.5, 2.0. 5.0 or 10.0. When a desired protein is not present in a control sample or a control mammal, inducing expression of a desired protein is achieved when any measurable level of the desired protein in the test sample or the test mammal is detected. One of ordinary skill in the art will understand appropriate assays to determine the level of protein expression in a sample, for example dot blots, northern blots, in situ hybridization, ELISA, immunoprecipitation, enzyme function, and phenotypic assays, or assays based on reporter proteins that can produce fluorescence or luminescence under appropriate conditions.

The phrase "inhibiting expression of a target gene" refers to the ability of a nucleic acid to silence, reduce, or inhibit the expression of a target gene. To examine the extent of gene silencing, a test sample (e.g. a sample of cells in culture expressing the target gene) or a test mammal (e.g. a mammal such as a human or an animal model such as a rodent (e.g. mouse) or a non-human primate (e.g. monkey) model) is contacted with a nucleic acid that silences, reduces, or inhibits expression of the target gene. Expression of the target gene in the test sample or test animal is compared to expression of the target gene in a control sample (e.g. a sample of cells in culture expressing the target gene) or a control mammal (e.g. a mammal such as a human or an animal model such as a rodent (e.g. mouse) or non-human primate (e.g. monkey) model) that is not contacted with or administered the nucleic acid. The expression of the target gene in a control sample or a control mammal may be assigned a value of 100%. In particular embodiments, silencing, inhibition, or reduction of expression of a target gene is achieved when the level of target gene expression in the test sample or the test mammal relative to the level of target gene expression in the control sample or the control mammal is about 95%, 90%, 85%, 80%, 75%, 70%, 65%, 60%, 55%, 50%, 45%, 40%, 35%, 30%, 25%, 20%, 15%, 10%, 5%, or 0%. In other words, the nucleic acids are capable of silencing, reducing, or inhibiting the expression of a target gene by at least about 5%, 10%, 15%, 20%, 25%, 30%, 35%, 40%, 45%, 50%, 55%, 60%, 65%, 70%, 75%, 80%, 85%, 90%, 95%, or 100% in a test sample or a test mammal relative to the level of target gene expression in a control sample or a control mammal not contacted with or administered the nucleic acid. Suitable assays for determining the level of target gene expression include, without limitation, examination of protein or mRNA levels using techniques known to those of skill in the art, such as, e.g., dot blots, northern blots, in situ hybridization, ELISA, immunoprecipitation, enzyme function, as well as phenotypic assays known to those of skill in the art.

An "effective amount" or "therapeutically effective amount" of an active agent or therapeutic agent such as a therapeutic nucleic acid is an amount sufficient to produce the desired effect, e.g. an increase or inhibition of expression of a target sequence in comparison to the normal expression level detected in the absence of the nucleic acid. An increase in expression of a target sequence is achieved when any measurable level is detected in the case of an expression product that is not present in the absence of the nucleic acid. In the case where the expression product is present at some level prior to contact with the nucleic acid, an in increase in expression is achieved when the fold increase in value obtained with a nucleic acid such as mRNA relative to control is about 1.05, 1.1, 1.2, 1.3, 1.4, 1.5, 1.75, 2, 2.5, 3, 4, 5, 6, 7, 8, 9, 10, 15, 20, 25, 30, 40, 50, 75, 100, 250, 500, 750, 1000, 5000, 10000 or greater. Inhibition of expression of a target gene or target sequence is achieved when the value obtained with a nucleic acid such as antisense oligonucleotide relative to the control is about 95%, 90%, 85%, 80%, 75%, 70%, 65%, 60%, 55%, 50%, 45%, 40%, 35%, 30%, 25%, 20%, 15%, 10%, 5%, or 0%. Suitable assays for measuring expression of a target gene or target sequence include, e.g., examination of protein or RNA levels using techniques known to those of skill in the art such as dot blots, northern blots, in situ hybridization, ELISA, immunoprecipitation, enzyme function, fluorescence or luminescence of suitable reporter proteins, as well as phenotypic assays known to those of skill in the art.

The term "nucleic acid" as used herein refers to a polymer containing at least two deoxyribonucleotides or ribonucleotides in either single- or double-stranded form and includes DNA, RNA, and hybrids thereof. DNA may be in the form of antisense molecules, plasmid DNA, cDNA, PCR products, or vectors. RNA may be in the form of small hairpin RNA (shRNA), messenger RNA (mRNA), antisense RNA, miRNA, micRNA, multivalent RNA, dicer substrate RNA or viral RNA (vRNA), and combinations thereof. Nucleic acids include nucleic acids containing known nucleotide analogs or modified backbone residues or linkages, which are synthetic, naturally occurring, and non-naturally occurring, and which have similar binding properties as the reference nucleic acid. Examples of such analogs include, without limitation, phosphorothioates, phosphoramidates, methyl phosphonates, chiral-methyl phosphonates, 2'-O-methyl ribonucleotides, and peptide-nucleic acids (PNAs). Unless specifically limited, the term encompasses nucleic acids containing known analogues of natural nucleotides that have similar binding properties as the reference nucleic acid. Unless otherwise indicated, a particular nucleic acid sequence also implicitly encompasses conservatively modified variants thereof (e.g., degenerate codon substitutions), alleles, orthologs, single nucleotide polymorphisms, and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., Nucleic Acid Res., 19:5081 (1991); Ohtsuka et al., J. Biol. Chem., 260:2605-2608 (1985); Rossolini et al., Mol. Cell. Probes, 8:91-98 (1994)). "Nucleotides" contain a sugar deoxyribose (DNA) or ribose (RNA), a base, and a phosphate group. Nucleotides are linked together through the phosphate groups. "Bases" include purines and pyrimidines, which further include natural compounds adenine, thymine, guanine, cytosine, uracil, inosine, and natural analogs, and synthetic derivatives of purines and pyrimidines, which include, but are not limited to, modifications which place new reactive groups such as, but not limited to, amines, alcohols, thiols, carboxylates, and alkylhalides.

The term "gene" refers to a nucleic acid (e.g., DNA or RNA) sequence that comprises partial length or entire length coding sequences necessary for the production of a polypeptide or precursor polypeptide.

"Gene product," as used herein, refers to a product of a gene such as an RNA transcript or a polypeptide.

The term "lipid" refers to a group of organic compounds that include, but are not limited to, esters of fatty acids and are generally characterized by being poorly soluble in water, but soluble in many organic solvents. They are usually divided into at least three classes: (1) "simple lipids," which include fats and oils as well as waxes; (2) "compound lipids," which include phospholipids and glycolipids; and (3) "derived lipids" such as steroids.

A "steroid" is a compound comprising the following carbon skeleton:

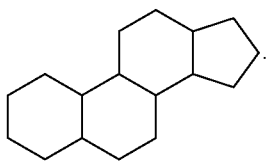 [SMILES: C1CCC2C(C1)CCC1C3CCCC3CCC21]

Non-limiting examples of steroids include cholesterol, and the like.

A "cationic lipid" refers to a lipid capable of being positively charged. Exemplary cationic lipids include one or more amine group(s) which bear the positive charge. Preferred cationic lipids are ionizable such that they can exist in a positively charged or neutral form depending on pH. The ionization of the cationic lipid affects the surface charge of the lipid nanoparticle under different pH conditions. This charge state can influence plasma protein absorption, blood clearance and tissue distribution (Semple, S. C., et al., Adv. Drug Deliv Rev 32:3-17 (1998)) as well as the ability to form endosomolytic non-bilayer structures (Hafez, I. M., et al., Gene Ther 8:1188-1196 (2001)) critical to the intracellular delivery of nucleic acids.

The term "polymer conjugated lipid" refers to a molecule comprising both a lipid portion and a polymer portion. An example of a polymer conjugated lipid is a pegylated lipid. The term "pegylated lipid" refers to a molecule comprising both a lipid portion and a polyethylene glycol portion. Pegylated lipids are known in the art and include 1-(monomethoxy-polyethyleneglycol)-2,3-dimyristoylglycerol (PEG-DMG) and the like.

The term "neutral lipid" refers to any of a number of lipid species that exist either in an uncharged or neutral zwitterionic form at a selected pH. At physiological pH, such lipids include, but are not limited to, phosphotidylcholines such as 1,2-Distearoyl-sn-glycero-3-phosphocholine (DSPC), 1,2-Dipalmitoyl-sn-glycero-3-phosphocholine (DPPC), 1,2-Dimyristoyl-sn-glycero-3-phosphocholine (DMPC), 1-Palmitoyl-2-oleoyl-sn-glycero-3-phosphocholine (POPC), 1,2-dioleoyl-sn-glycero-3-phosphocholine (DOPC), phophatidylethanolamines such as 1,2-Dioleoyl-sn-glycero-3-phosphoethanolamine (DOPE), sphingomyelins (SM), ceramides, steroids such as sterols and their derivatives. Neutral lipids may be synthetic or naturally derived.

The term "charged lipid" refers to any of a number of lipid species that exist in either a positively charged or negatively charged form independent of the pH within a useful physiological range e.g. pH 3 to pH 9. Charged lipids may be synthetic or naturally derived. Examples of charged lipids include phosphatidylserines, phosphatidic acids, phosphatidylglycerols, phosphatidylinositols, sterol hemisuccinates, dialkyl trimethylammonium-propanes, (e.g. DOTAP, DOTMA), dialkyl dimethylaminopropanes, ethyl phosphocholines, dimethylaminoethane carbamoyl sterols (e.g. DC-Chol).

The term "lipid nanoparticle" refers to particles having at least one dimension on the order of nanometers (e.g., 1-1,000 nm) which include one or more of the compounds of structure (I) or other specified cationic lipids. In some embodiments, lipid nanoparticles are included in a formulation that can be used to deliver an active agent or therapeutic agent, such as a nucleic acid (e.g., mRNA) to a target site of interest (e.g., cell, tissue, organ, tumor, and the like). In some embodiments, the lipid nanoparticles of the invention comprise a nucleic acid. Such lipid nanoparticles typically comprise a compound of structure (I) and one or more excipient selected from neutral lipids, charged lipids, steroids and polymer conjugated lipids. In some embodiments, the active agent or therapeutic agent, such as a nucleic acid, may be encapsulated in the lipid portion of the lipid nanoparticle or an aqueous space enveloped by some or all of the lipid portion of the lipid nanoparticle, thereby protecting it from enzymatic degradation or other undesirable effects induced by the mechanisms of the host organism or cells e.g. an adverse immune response.

In various embodiments, the lipid nanoparticles have a mean diameter of from about 30 nm to about 150 nm, from about 40 nm to about 150 nm, from about 50 nm to about 150 nm, from about 60 nm to about 130 nm, from about 70 nm to about 110 nm, from about 70 nm to about 100 nm, from about 80 nm to about 100 nm, from about 90 nm to about 100 nm, from about 70 to about 90 nm, from about 80 nm to about 90 nm, from about 70 nm to about 80 nm, or about 30 nm, 35 nm, 40 nm, 45 nm, 50 nm, 55 nm, 60 nm, 65 nm, 70 nm, 75 nm, 80 nm, 85 nm, 90 nm, 95 nm, 100 nm, 105 nm, 110 nm, 115 nm, 120 nm, 125 nm, 130 nm, 135 nm, 140 nm, 145 nm, or 150 nm, and are substantially non-toxic. In certain embodiments, nucleic acids, when present in the lipid nanoparticles, are resistant in aqueous solution to degradation with a nuclease. Lipid nanoparticles comprising nucleic acids and their method of preparation are disclosed in, e.g., U.S. Patent Publication Nos. 2004/0142025, 2007/0042031 and PCT Pub. Nos. WO 2017/004143, WO 2015/199952, WO 2013/016058 and WO 2013/086373, the full disclosures of which are herein incorporated by reference in their entirety for all purposes.

As used herein, "lipid encapsulated" refers to a lipid nanoparticle that provides an active agent or therapeutic agent, such as a nucleic acid (e.g., mRNA), with full encapsulation, partial encapsulation, or both. In an embodiment, the nucleic acid (e.g., mRNA) is fully encapsulated in the lipid nanoparticle.

As used herein, the term "aqueous solution" refers to a composition comprising water.

"Serum-stable" in relation to nucleic acid-lipid nanoparticles means that the nucleotide is not significantly degraded after exposure to a serum or nuclease assay that would significantly degrade free DNA or RNA. Suitable assays include, for example, a standard serum assay, a DNAse assay, or an RNAse assay.

"Systemic delivery," as used herein, refers to delivery of a therapeutic product that can result in a broad exposure of an active agent within an organism. Some techniques of administration can lead to the systemic delivery of certain agents, but not others. Systemic delivery means that a useful, preferably therapeutic, amount of an agent is exposed to most parts of the body. Systemic delivery of lipid nanoparticles can be by any means known in the art including, for example, intravenous, intraarterial, subcutaneous, and intraperitoneal delivery. In some embodiments, systemic delivery of lipid nanoparticles is by intravenous delivery.

"Local delivery," as used herein, refers to delivery of an active agent directly to a target site within an organism. For example, an agent can be locally delivered by direct injection into a disease site such as a tumor, other target site such as a site of inflammation, or a target organ such as the liver, heart, pancreas, kidney, and the like. Local delivery can also include topical applications or localized injection techniques such as intramuscular, subcutaneous or intradermal injection. Local delivery does not preclude a systemic pharmacological effect.

"Alkyl" refers to a straight or branched hydrocarbon chain radical consisting solely of carbon and hydrogen atoms, which is saturated, having, for example, from one to twenty-four carbon atoms ($C_1$-$C_{24}$ alkyl), six to twenty-four carbon atoms ($C_6$-$C_{24}$ alkyl), four to twenty carbon atoms ($C_4$-$C_{20}$ alkyl), six to sixteen carbon atoms ($C_6$-$C_{16}$ alkyl), six to nine carbon atoms ($C_6$-$C_9$ alkyl), one to fifteen carbon atoms ($C_1$-$C_{15}$ alkyl), one to twelve carbon atoms ($C_1$-$C_{12}$ alkyl), one to eight carbon atoms ($C_1$-$C_8$ alkyl) or one to six carbon atoms ($C_1$-$C_6$ alkyl) and which is attached to the rest of the molecule by a single bond, e.g., methyl, ethyl, n-propyl, 1 methylethyl (iso propyl), n-butyl, n-pentyl, 1,1-dimethylethyl (t butyl), 3-methylhexyl, 2-methylhexyl, and the like. Unless stated otherwise specifically in the specification, an alkyl group is optionally substituted.

"Alkenyl" refers to a straight or branched hydrocarbon chain radical consisting solely of carbon and hydrogen atoms, which contains one or more carbon-carbon double bonds, and having, for example, from two to twenty-four carbon atoms ($C_2$-$C_{24}$ alkenyl), six to twenty-four carbon atoms ($C_6$-$C_{24}$ alkenyl), four to twenty carbon atoms ($C_4$-$C_{20}$ alkenyl), six to sixteen carbon atoms ($C_6$-$C_{16}$ alkenyl), six to nine carbon atoms ($C_6$-$C_9$ alkenyl), two to fifteen carbon atoms ($C_2$-$C_{15}$ alkenyl), two to twelve carbon atoms ($C_2$-$C_{12}$ alkenyl), two to eight carbon atoms ($C_2$-$C_8$ alkenyl) or two to six carbon atoms ($C_2$-$C_6$ alkenyl) and which is attached to the rest of the molecule by a single bond, e.g., ethenyl, prop-1-enyl, but-1-enyl, pent-1-enyl, penta-1,4-dienyl, and the like. Unless stated otherwise specifically in the specification, an alkenyl group is optionally substituted.

"Alkylene" or "alkylene chain" refers to a straight or branched divalent hydrocarbon chain linking the rest of the molecule to a radical group, consisting solely of carbon and hydrogen, which is saturated, and having, for example, from one to twenty-four carbon atoms ($C_1$-$C_{24}$ alkylene), one to fifteen carbon atoms ($C_1$-$C_{15}$ alkylene), one to twelve carbon atoms ($C_1$-$C_{12}$ alkylene), one to eight carbon atoms ($C_1$-$C_8$ alkylene), one to six carbon atoms ($C_1$-$C_6$ alkylene), two to four carbon atoms ($C_2$-$C_4$ alkylene), one to two carbon atoms ($C_1$-$C_2$ alkylene), e.g., methylene, ethylene, propylene, n-butylene, and the like. The alkylene chain is attached to the rest of the molecule through a single bond and to the radical group through a single bond. The points of attachment of the alkylene chain to the rest of the molecule and to the radical group can be through one carbon or any two carbons within the chain. Unless stated otherwise specifically in the specification, an alkylene chain may be optionally substituted.

"Alkenylene" or "alkenylene chain" refers to a straight or branched divalent hydrocarbon chain linking the rest of the molecule to a radical group, consisting solely of carbon and hydrogen, which contains one or more carbon-carbon double bonds, and having, for example, from two to twenty-four carbon atoms ($C_2$-$C_{24}$ alkenylene), two to fifteen carbon atoms ($C_2$-$C_{15}$ alkenylene), two to twelve carbon atoms ($C_2$-$C_{12}$ alkenylene), two to eight carbon atoms ($C_2$-$C_8$ alkenylene), two to six carbon atoms ($C_2$-$C_6$ alkenylene) or two to four carbon atoms ($C_2$-$C_4$ alkenylene), e.g., ethenylene, propenylene, n-butenylene, and the like. The alkenylene chain is attached to the rest of the molecule through a single or double bond and to the radical group through a single or double bond. The points of attachment of the alkenylene chain to the rest of the molecule and to the radical group can be through one carbon or any two carbons within the chain. Unless stated otherwise specifically in the specification, an alkenylene chain may be optionally substituted.

"Heteroalkylene" refers to an alkylene as defined herein, wherein at least one carbon-carbon bond within the alkylene is replaced by a carbon-heteroatom-carbon bond. Heteroatoms include O, N and S. An exemplary heteroalkylene is aminylheteroalkylene, which is a heteroalkylene wherein the heteroatom is N (e.g., —NR—, wherein R is H or $C_1$-$C_{12}$ alkyl). Other heteroalkylenes include alkylene oxides, such as ethylene oxides and polyethylene oxides. Heteroalkylenes include one to twenty-four carbon atoms ($C_1$-$C_{24}$ heteroalkylene), one to fifteen carbon atoms ($C_1$-$C_{15}$ heteroalkylene), one to twelve carbon atoms ($C_1$-$C_{12}$ heteroalkylene), one to eight carbon atoms ($C_1$-$C_8$ heteroalkylene), one to six carbon atoms ($C_1$-$C_6$ heteroalkylene), two to four carbon atoms (heteroalkylene), one to two carbon atoms ($C_1$-$C_2$ heteroalkylene), and the like. The heteroalkylene chain is attached to the rest of the molecule through a single bond and to the radical group through a single bond. The points of attachment of the heteroalkylene chain to the rest of the molecule and to the radical group can be through one carbon or any two carbons within the chain. Unless stated otherwise specifically in the specification, a heteroalkylene chain may be optionally substituted.

"Heteroalkenylene" is a heteroalkylene as defined herein, comprising at least on carbon-carbon double bond. Heteroalkenylenes include from two to twenty-four carbon atoms ($C_2$-$C_{24}$ heteroalkenylene), two to fifteen carbon atoms ($C_2$-$C_{15}$ heteroalkenylene), two to twelve carbon atoms ($C_2$-$C_{12}$ heteroalkenylene), two to eight carbon atoms ($C_2$-$C_8$ heteroalkenylene), two to six carbon atoms ($C_2$-$C_6$ heteroalkenylene) or two to four carbon atoms ($C_2$-$C_4$ heteroalkenylene), and the like. The heteroalkenylene chain is attached to the rest of the molecule through a single or double bond and to the radical group through a single or double bond. The points of attachment of the heteroalkenylene chain to the rest of the molecule and to the radical group can be through one carbon or any two carbons within the chain. Unless stated otherwise specifically in the specification, a heteroalkenylene chain may be optionally substituted.

The term "substituted" used herein means any of the above groups (e.g. alkyl, alkenyl, alkylene, alkenylene, heteroalkylene and heteroalkenylene) wherein at least one hydrogen atom is replaced by a bond to a non-hydrogen atom such as, but not limited to: a halogen atom such as F, Cl, Br, or I; oxo groups (=O); hydroxyl groups (—OH); $C_1$-$C_{12}$ alkyl groups; cycloalkyl groups; —C(=O)OR'; —O(C=O)R'; —C(=O)R'; —OR'; —S(O)$_x$R'; —S—SR'; —C(=O)SR'; —SC(=O)R'; —NR'R'; —NR'C(=O)R'; —C(=O)NR'R'; —NR'C(=O)NR'R'; —OC(=O)NR'R'; —NR'C(=O)OR'; —NRS(O)$_x$NR'R'; —NR'S(O)$_x$R'; and —S(O)$_x$NR'R', wherein: R' is, at each occurrence, independently H, $C_1$-$C_{15}$ alkyl or cycloalkyl, and x is 0, 1 or 2. In some embodiments the substituent is a $C_1$-$C_{12}$ alkyl group. In other embodiments, the substituent is a cycloalkyl group. In other embodiments, the substituent is a halo group, such as fluoro. In other embodiments, the substituent is an oxo group. In other embodiments, the substituent is a hydroxyl group. In other embodiments, the substituent is an alkoxy group (—OR'). In other embodiments, the substituent is a carboxyl group. In other embodiments, the substituent is an amine group (—NR'R').

"Optional" or "optionally" (e.g., optionally substituted) means that the subsequently described event of circumstances may or may not occur, and that the description includes instances where said event or circumstance occurs and instances in which it does not. For example, "optionally substituted alkyl" means that the alkyl radical may or may not be substituted and that the description includes both substituted alkyl radicals and alkyl radicals having no substitution.

"Prodrug" is meant to indicate a compound that may be converted under physiological conditions or by solvolysis to a biologically active compound of structure (I). Thus, the term "prodrug" refers to a metabolic precursor of a compound of structure (I) that is pharmaceutically acceptable. A prodrug may be inactive when administered to a subject in need thereof, but is converted in vivo to an active compound of structure (I). Prodrugs are typically rapidly transformed in vivo to yield the parent compound of structure (I), for example, by hydrolysis in blood. The prodrug compound often offers advantages of solubility, tissue compatibility or delayed release in a mammalian organism (see, Bundgard, H., Design of Prodrugs (1985), pp. 7-9, 21-24 (Elsevier, Amsterdam)). A discussion of prodrugs is provided in Higuchi, T., et al., A.C.S. Symposium Series, Vol. 14, and in Bioreversible Carriers in Drug Design, Ed. Edward B. Roche, American Pharmaceutical Association and Pergamon Press, 1987.

The term "prodrug" is also meant to include any covalently bonded carriers, which release the active compound of structure (I) in vivo when such prodrug is administered to a mammalian subject. Prodrugs of a compound of structure (I) may be prepared by modifying functional groups present in the compound of structure (I) in such a way that the modifications are cleaved, either in routine manipulation or in vivo, to the parent compound of structure (I). Prodrugs include compounds of structure (I) wherein a hydroxy, amino or mercapto group is bonded to any group that, when the prodrug of the compound of structure (I) is administered to a mammalian subject, cleaves to form a free hydroxy, free amino or free mercapto group, respectively. Examples of prodrugs include, but are not limited to, acetate, formate and benzoate derivatives of alcohol or amide derivatives of amine functional groups in the compounds of structure (I) and the like.

Embodiments of the invention disclosed herein are also meant to encompass all pharmaceutically acceptable compounds of the compound of structure (I) being isotopically-labelled by having one or more atoms replaced by an atom having a different atomic mass or mass number. Examples of isotopes that can be incorporated into the disclosed compounds include isotopes of hydrogen, carbon, nitrogen, oxygen, phosphorous, fluorine, chlorine, and iodine, such as $^2H$, $^3H$, $^{11}C$, $^{13}C$, $^{14}C$, $^{13}N$, $^{15}N$, $^{15}O$, $^{17}O$, $^{18}O$, $^{31}P$, $^{32}P$, $^{35}S$, $^{18}F$, $^{36}Cl$, $^{123}I$, and $^{125}I$, respectively. These radiolabeled compounds could be useful to help determine or measure the effectiveness of the compounds, by characterizing, for example, the site or mode of action, or binding affinity to pharmacologically important site of action. Certain isotopically-labelled compounds of structure (I) or (II), for example, those incorporating a radioactive isotope, are useful in drug and/or substrate tissue distribution studies. The radioactive isotopes tritium, i.e., $^3H$, and carbon-14, i.e., $^{14}C$, are particularly useful for this purpose in view of their ease of incorporation and ready means of detection.

Substitution with heavier isotopes such as deuterium, i.e., $^2H$, may afford certain therapeutic advantages resulting from greater metabolic stability, for example, increased in vivo half-life or reduced dosage requirements, and hence may be preferred in some circumstances.

Substitution with positron emitting isotopes, such as $^{11}C$, $^{18}F$, $^{15}O$ and $^{13}N$, can be useful in Positron Emission Topography (PET) studies for examining substrate receptor occupancy. Isotopically-labeled compounds of structure (I) can generally be prepared by conventional techniques known to those skilled in the art or by processes analogous to those described in the Preparations and Examples as set out below using an appropriate isotopically-labeled reagent in place of the non-labeled reagent previously employed.

Embodiments of the invention disclosed herein are also meant to encompass the in vivo metabolic products of the disclosed compounds. Such products may result from, for example, the oxidation, reduction, hydrolysis, amidation, esterification, and the like of the administered compound, primarily due to enzymatic processes. Accordingly, embodiments of the invention include compounds produced by a process comprising administering a compound of this invention to a mammal for a period of time sufficient to yield a metabolic product thereof. Such products are typically identified by administering a radiolabeled compound of structure (I) in a detectable dose to an animal, such as rat, mouse, guinea pig, monkey, or to human, allowing sufficient time for metabolism to occur, and isolating its conversion products from the urine, blood or other biological samples.

"Stable compound" and "stable structure" are meant to indicate a compound that is sufficiently robust to survive isolation to a useful degree of purity from a reaction mixture, and formulation into an efficacious therapeutic agent.

"Mammal" includes humans and both domestic animals such as laboratory animals and household pets (e.g., cats, dogs, swine, cattle, sheep, goats, horses, rabbits), and non-domestic animals such as wildlife and the like.

"Pharmaceutically acceptable carrier, diluent or excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

"Pharmaceutically acceptable salt" includes both acid and base addition salts.

"Pharmaceutically acceptable acid addition salt" refers to those salts which retain the biological effectiveness and properties of the free bases, which are not biologically or otherwise undesirable, and which are formed with inorganic acids such as, but are not limited to, hydrochloric acid, hydrobromic acid, sulfuric acid, nitric acid, phosphoric acid and the like, and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid, undecylenic acid, and the like.

"Pharmaceutically acceptable base addition salt" refers to those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, deanol, 2-dimethylaminoethanol, 2-diethylaminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, N-ethylpiperidine, polyamine resins and the like. Particularly preferred organic bases are isopropylamine, diethylamine, ethanolamine, trimethylamine, dicyclohexylamine, choline and caffeine.

Often crystallizations produce a solvate of the compound of structure (I). As used herein, the term "solvate" refers to an aggregate that comprises one or more molecules of a compound of structure (I) with one or more molecules of solvent. The solvent may be water, in which case the solvate may be a hydrate. Alternatively, the solvent may be an organic solvent. Thus, the compounds of the present invention may exist as a hydrate, including a monohydrate, dihydrate, hemihydrate, sesquihydrate, trihydrate, tetrahydrate and the like, as well as the corresponding solvated forms. In some embodiments, the compound of structure (I) may exist as a true solvate, while in other cases, the compound of structure (I) may merely retain adventitious water or be a mixture of water plus some adventitious solvent.

A "pharmaceutical composition" refers to a formulation of a compound of structure (I) and a medium generally accepted in the art for the delivery of the biologically active compound to mammals, e.g., humans. Such a medium includes all pharmaceutically acceptable carriers, diluents or excipients therefor.

"Effective amount" or "therapeutically effective amount" refers to that amount of a compound of structure (I) which, when administered to a mammal, preferably a human, is sufficient to effect treatment in the mammal, preferably a human. The amount of a lipid nanoparticle of embodiments the invention which constitutes a "therapeutically effective amount" will vary depending on the compound, the condition and its severity, the manner of administration, and the age of the mammal to be treated, but can be determined routinely by one of ordinary skill in the art having regard to his own knowledge and to this disclosure.

"Treating" or "treatment" as used herein covers the treatment of the disease or condition of interest in a mammal, preferably a human, having the disease or condition of interest, and includes:

(i) preventing the disease or condition from occurring in a mammal, in particular, when such mammal is predisposed to the condition but has not yet been diagnosed as having it;

(ii) inhibiting the disease or condition, i.e., arresting its development; (iii) relieving the disease or condition, i.e., causing regression of the disease or condition; or (iv) relieving the symptoms resulting from the disease or condition, i.e., relieving pain without addressing the underlying disease or condition. As used herein, the terms "disease" and "condition" may be used interchangeably or may be different in that the particular malady or condition may not have a known causative agent (so that etiology has not yet been worked out) and it is therefore not yet recognized as a disease but only as an undesirable condition or syndrome, wherein a more or less specific set of symptoms have been identified by clinicians.

The compounds of structure (I), or their pharmaceutically acceptable salts may contain one or more asymmetric centers and may thus give rise to enantiomers, diastereomers, and other stereoisomeric forms that may be defined, in terms of absolute stereochemistry, as (R)- or (S)- or, as (D)- or (L)- for amino acids. Embodiments of the present invention are meant to include all such possible isomers, as well as their racemic and optically pure forms. Optically active (+) and (−), (R)- and (S)-, or (D)- and (L)-isomers may be prepared using chiral synthons or chiral reagents, or resolved using conventional techniques, for example, chromatography and fractional crystallization. Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). When the compounds described herein contain olefinic double bonds or other centers of geometric asymmetry, and unless specified otherwise, it is intended that the compounds include both E and Z geometric isomers. Likewise, all tautomeric forms are also intended to be included.

A "stereoisomer" refers to a compound made up of the same atoms bonded by the same bonds but having different three-dimensional structures, which are not interchangeable. The present invention contemplates various stereoisomers and mixtures thereof and includes "enantiomers", which refers to two stereoisomers whose molecules are nonsuperimposeable mirror images of one another.

A "tautomer" refers to a proton shift from one atom of a molecule to another atom of the same molecule. The present invention includes tautomers of any said compounds.

Compounds

In an aspect, the invention provides novel lipid compounds which are capable of combining with other lipid components such as neutral lipids, charged lipids, steroids and/or polymer conjugated-lipids to form lipid nanoparticles with oligonucleotides. Without wishing to be bound by theory, it is thought that these lipid nanoparticles shield oligonucleotides from degradation in the serum and provide for effective delivery of oligonucleotides to cells in vitro and in vivo.

In one embodiment, the compounds have the following structure (I):

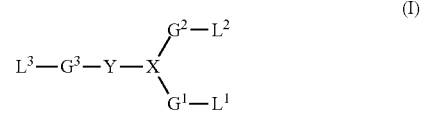

(I)

or a pharmaceutically acceptable salt, prodrug or stereoisomer thereof, wherein:

X is N, and Y is absent; or X is CR, and Y is NR;

$L^1$ is —O(C=O)$R^1$, —(C=O)O$R^1$, —C(=O)$R^1$, —O$R^1$, —S(O)$_x$$R^1$, —S—S$R^1$, —C(=O)S$R^1$, —SC(=O)$R^1$, —N$R^a$C(=O)$R^1$, —C(=O)N$R^b$$R^c$, —N$R^a$C(=O)N$R^b$$R^c$, —OC(=O)N$R^b$$R^c$ or —N$R^a$C(=O)O$R^1$;

$L^2$ is —O(C=O)$R^2$, —(C=O)O$R^2$, —C(=O)$R^2$, —O$R^2$, —S(O)$_x$$R^2$, —S—S$R^2$, —C(=O)S$R^2$, —SC(=O)$R^2$, —N$R^d$C(=O)$R^2$, —C(=O)N$R^e$$R^f$, —N$R^d$C(=O)N$R^e$$R^f$, —OC(=O)N$R^e$$R^f$; —N$R^d$C(=O)O$R^2$ or a direct bond to $R^2$;

$L^3$ is —O(C=O)$R^3$ or —(C=O)O$R^3$;

$G^1$ and $G^2$ are each independently $C_2$-$C_{12}$ alkylene or $C_2$-$C_{12}$ alkenylene;

$G^3$ is $C_1$-$C_{24}$ alkylene, $C_2$-$C_{24}$ alkenylene, $C_1$-$C_{24}$ heteroalkylene or $C_2$-$C_{24}$ heteroalkenylene;

$R^a$, $R^b$, $R^d$ and $R^e$ are each independently H or $C_1$-$C_{12}$ alkyl or $C_1$-$C_{12}$ alkenyl;

$R^c$ and $R^f$ are each independently $C_1$-$C_{12}$ alkyl or $C_2$-$C_{12}$ alkenyl;

each R is independently H or Q-$C_{12}$ alkyl;

$R^1$, $R^2$ and $R^3$ are each independently $C_1$-$C_{24}$ alkyl or $C_2$-$C_{24}$ alkenyl; and x is 0, 1 or 2, and wherein each alkyl, alkenyl, alkylene, alkenylene, heteroalkylene and heteroalkenylene is independently substituted or unsubstituted unless otherwise specified.

In more embodiments of structure (I):

X is N, and Y is absent; or X is CR, and Y is NR;

$L^1$ is —O(C=O)$R^1$, —(C=O)O$R^1$, —C(=O)$R^1$, —O$R^1$, —S(O)$_x$$R^1$, —S—S$R^1$, —C(=O)S$R^1$, —SC(=O)$R^1$, —N$R^a$C(=O)$R^1$, —C(=O)N$R^b$$R^c$, —N$R^a$C(=O)N$R^b$$R^c$, —OC(=O)N$R^b$$R^c$ or —N$R^a$C(=O)O$R^1$;

$L^2$ is —O(C=O)$R^2$, —(C=O)O$R^2$, —C(=O)$R^2$, —O$R^2$, —S(O)$_x$$R^2$, —S—S$R^2$, —C(=O)S$R^2$, —SC(=O)$R^2$, —N$R^d$C(=O)$R^2$, —C(=O)N$R^e$$R^f$, —N$R^d$C(=O)N$R^e$$R^f$, —OC(=O)N$R^e$$R^f$; —N$R^d$C(=O)O$R^2$ or a direct bond to $R^2$;

$L^3$ is —O(C=O)$R^3$ or —(C=O)O$R^3$;

$G^1$ and $G^2$ are each independently $C_2$-$C_{12}$ alkylene or $C_2$-$C_{12}$ alkenylene;

$G^3$ is $C_1$-$C_{24}$ alkylene, $C_2$-$C_{24}$ alkenylene, $C_1$-$C_{24}$ heteroalkylene or $C_2$-$C_{24}$ heteroalkenylene when X is CR, and Y is NR; and $G^3$ is $C_1$-$C_{24}$ heteroalkylene or $C_2$-$C_{24}$ heteroalkenylene when X is N, and Y is absent;

$R^a$, $R^b$, $R^d$ and $R^e$ are each independently H or $C_1$-$C_{12}$ alkyl or $C_1$-$C_{12}$ alkenyl;

$R^c$ and $R^f$ are each independently $C_1$-$C_{12}$ alkyl or $C_2$-$C_{12}$ alkenyl;

each R is independently H or $C_1$-$C_{12}$ alkyl;

$R^1$, $R^2$ and $R^3$ are each independently $C_1$-$C_{24}$ alkyl or $C_2$-$C_{24}$ alkenyl; and x is 0, 1 or 2, and wherein each alkyl, alkenyl, alkylene, alkenylene, heteroalkylene and heteroalkenylene is independently substituted or unsubstituted unless otherwise specified.

In other embodiments of structure (I):

X is N and Y is absent, or X is CR and Y is NR;

$L^1$ is —O(C=O)$R^1$, —(C=O)O$R^1$, —C(=O)$R^1$, —O$R^1$, —S(O)$_x$$R^1$, —S—S$R^1$, —C(=O)S$R^1$, —SC(=O)$R^1$, —N$R^a$C(=O)$R^1$, —C(=O)N$R^b$$R^c$, —N$R^a$C(=O)N$R^b$$R^c$, —OC(=O)N$R^b$$R^c$ or —N$R^a$C(=O)O$R'$;

$L^2$ is —O(C=O)$R^2$, —(C=O)O$R^2$, —C(=O)$R^2$, —O$R^2$, —S(O)$_x$$R^2$, —S—S$R^2$, —C(=O)S$R^2$, —SC(=O)$R^2$, —N$R^d$C(=O)$R^2$, —C(=O)N$R^e$$R^f$, —N$R^d$C(=O)N$R^e$$R^f$, —OC(=O)N$R^e$$R^f$; —N$R^d$C(=O)O$R^2$ or a direct bond to $R^2$;

$L^3$ is —O(C=O)$R^3$ or —(C=O)O$R^3$;

$G^1$ and $G^2$ are each independently $C_2$-$C_{12}$ alkylene or $C_2$-$C_{12}$ alkenylene;

$G^3$ is $C_1$-$C_{24}$ alkylene, $C_2$-$C_{24}$ alkenylene, $C_1$-$C_{24}$ heteroalkylene or $C_2$-$C_{24}$ heteroalkenylene;

$R^a$, $R^b$, $R^d$ and $R^e$ are each independently H or $C_1$-$C_{12}$ alkyl or $C_1$-$C_{12}$ alkenyl;

$R^c$ and $R^f$ are each independently $C_1$-$C_{12}$ alkyl or $C_2$-$C_{12}$ alkenyl;

each R is independently H or $C_1$-$C_{12}$ alkyl;

$R^1$, $R^2$ and $R^3$ are each independently branched $C_6$-$C_{24}$ alkyl or branched $C_6$-$C_{24}$ alkenyl; and x is 0, 1 or 2, and wherein each alkyl, alkenyl, alkylene, alkenylene, heteroalkylene and heteroalkenylene is independently substituted or unsubstituted unless otherwise specified.

In certain embodiments, $G^3$ is unsubstituted. In more specific embodiments $G^3$ is $C_2$-$C_{12}$ alkylene, tor example, in some embodiments $G^3$ is $C_3$-$C_7$ alkylene or in other embodiments G is $C_3$-$C_{12}$ alkylene. In some embodiments, G is $C_2$ or $C_3$ alkylene.

In other embodiments, $G^3$ is $C_1$-$C_{12}$ heteroalkylene, for example $C_1$-$C_{12}$ aminylalkylene.

In certain embodiments, X is N and Y is absent. In other embodiments, X is CR and Y is NR, for example in some of these embodiments R is H.

In some of the foregoing embodiments, the compound has one of the following structures (IA), (IB), (IC) or (ID):

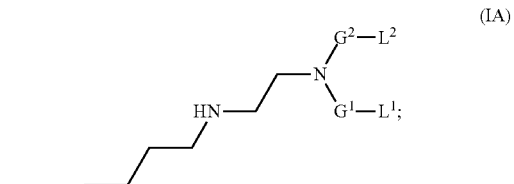

(IA)

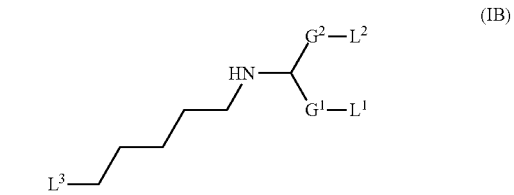

(IB)

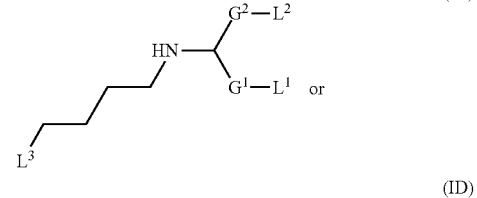

(IC)

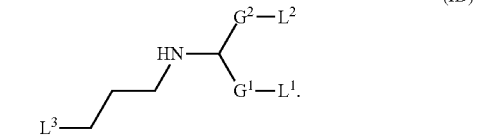

(ID)

In some of the foregoing embodiments, $L^1$ is —O(C=O)$R^1$, —(C=O)O$R^1$ or —C(=O)N$R^b$$R^c$, and $L^2$ is —O(C=O)$R^2$, —(C=O)O$R^2$ or —C(=O)N$R^e$$R^f$. In other specific embodiments, $L^1$ is —(C=O)O$R'$ and $L^2$ is —(C=O)O$R^2$. In any of the foregoing embodiments, $L^3$ is —(C=O)O$R^3$.

In some of the foregoing embodiments, $G^1$ and $G^2$ are each independently $C_2$-$C_{12}$ alkylene, for example $C_4$-$C_{10}$ alkylene.

In some of the foregoing embodiments, $R^1$, $R^2$ and $R^3$ are each, independently branched $C_6$-$C_{24}$ alkyl. For example, in some embodiments, $R^1$, $R^2$ and $R^3$ each, independently have the following structure:

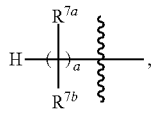

wherein:

$R^{7a}$ and $R^{7b}$ are, at each occurrence, independently H or $C_1$-$C_{12}$ alkyl; and a is an integer from 2 to 12, wherein $R^{7a}$, $R^{7b}$ and a are each selected such that $R^1$ and $R^2$ each independently comprise from 6 to 20 carbon atoms. For example, in some embodiments a is an integer ranging from 5 to 9 or from 8 to 12.

In some of the foregoing embodiments, at least one occurrence of $R^{7a}$ is H. For example, in some embodiments, $R^{7a}$ is H at each occurrence. In other different embodiments of the foregoing, at least one occurrence of $R^{7b}$ is $C_1$-$C_8$ alkyl. For example, in some embodiments, $C_1$-$C_8$ alkyl is methyl, ethyl, n-propyl, iso-propyl, n-butyl, iso-butyl, tert-butyl, n-hexyl or n-octyl.

In some of the foregoing embodiments, X is CR, Y is NR and $R^3$ is $C_1$-$C_{12}$ alkyl, such as ethyl, propyl or butyl. In some of these embodiments, $R^1$ and $R^2$ are each independently branched $C_6$-$C_{24}$ alkyl.

In different embodiments, $R^1$, $R^2$ and $R^3$ each, independently have one of the following structures:

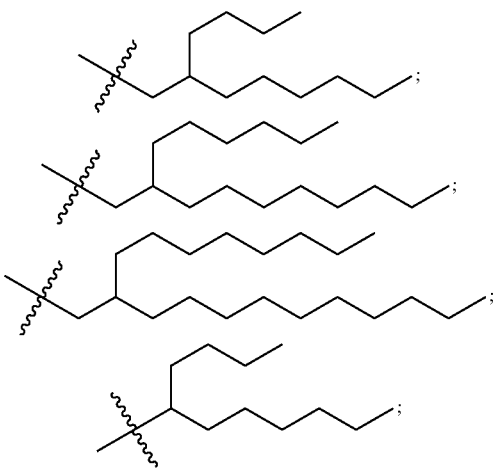

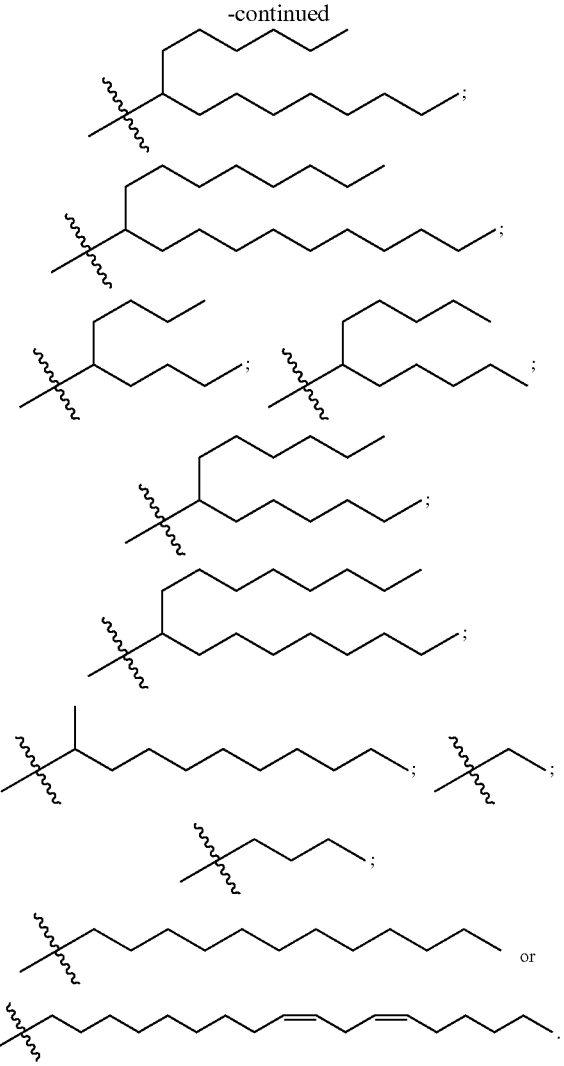

In certain embodiments, $R^1$ and $R^2$ and $R^3$ are each, independently, branched $C_6$-$C_{24}$ alkyl and $R^3$ is $C_1$-$C_{24}$ alkyl or $C_2$-$C_{24}$ alkenyl.

In some of the foregoing embodiments, $R^b$, $R^c$, $R^e$ and $R^f$ are each independently $C_3$-$C_{12}$ alkyl. For example, in some embodiments $R^b$, $R^c$, $R^e$ and $R^f$ are n-hexyl and in other embodiments $R^b$, $R^c$, $R^e$ and $R^f$ are n-octyl.

In various different embodiments, the compound has one of the structures set forth in Table 1 below.

TABLE 1

Representative Compounds

| No. | Structure |
|---|---|
| 1 | 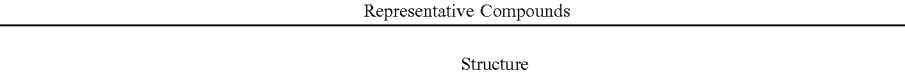 |

TABLE 1-continued

Representative Compounds

| No. | Structure |
|---|---|
| 2 | 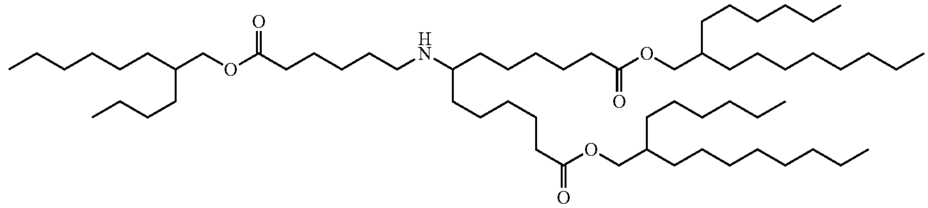 [SMILES: CCCCCCCCC(CCCCCC)COC(=O)CCCCCC(CCCCCC(=O)OCC(CCCCCC)CCCCCCCC)NCCCCCC(=O)OCC(CCCC)CCCCCC] |
| 3 | 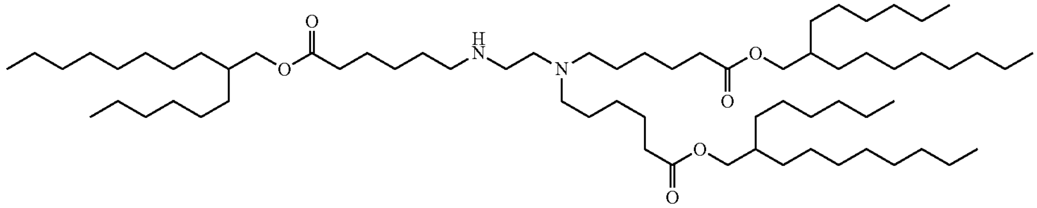 [SMILES: CCCCCCCCC(CCCCCC)COC(=O)CCCCCNCCN(CCCCCC(=O)OCC(CCCCCC)CCCCCCCC)CCCCCC(=O)OCC(CCCCCC)CCCCCCCC] |
| 4 | 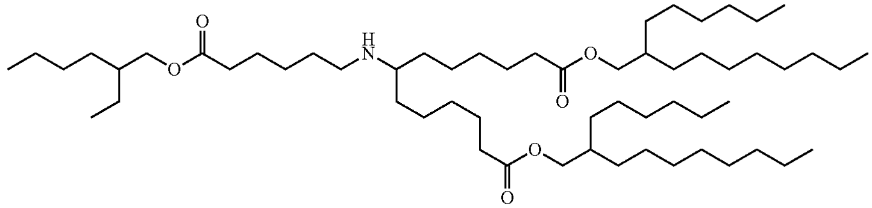 [SMILES: CCCCCCCCC(CCCCCC)COC(=O)CCCCCC(CCCCCC(=O)OCC(CCCCCC)CCCCCCCC)NCCCCCC(=O)OCC(CC)CCCC] |
| 5 | 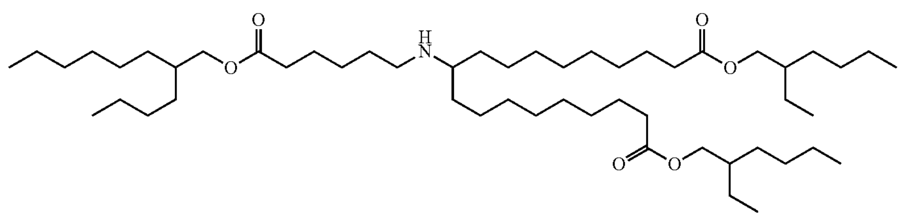 [SMILES: CCCCCCC(CCCC)COC(=O)CCCCCNC(CCCCCCCCC(=O)OCC(CC)CCCC)CCCCCCCCC(=O)OCC(CC)CCCC] |
| 6 | 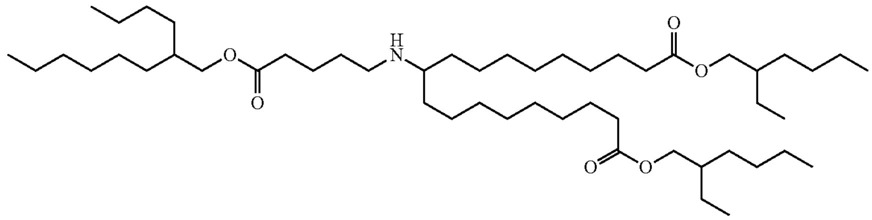 [SMILES: CCCCCCC(CCCC)COC(=O)CCCCNC(CCCCCCCCC(=O)OCC(CC)CCCC)CCCCCCCCC(=O)OCC(CC)CCCC] |
| 7 | 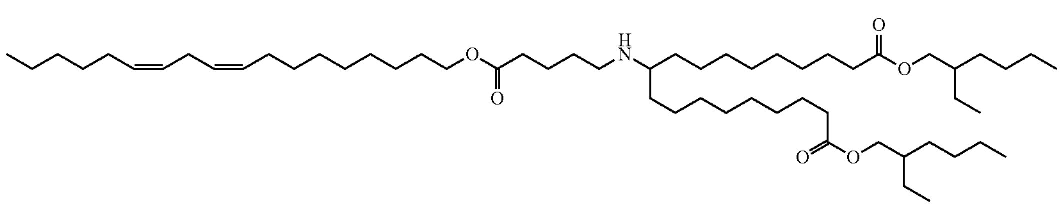 [SMILES: CCCCC/C=C\C/C=C\CCCCCCCCOC(=O)CCCCNC(CCCCCCCCC(=O)OCC(CC)CCCC)CCCCCCCCC(=O)OCC(CC)CCCC] |

TABLE 1-continued

Representative Compounds

| No. | Structure |
|---|---|
| 8 | 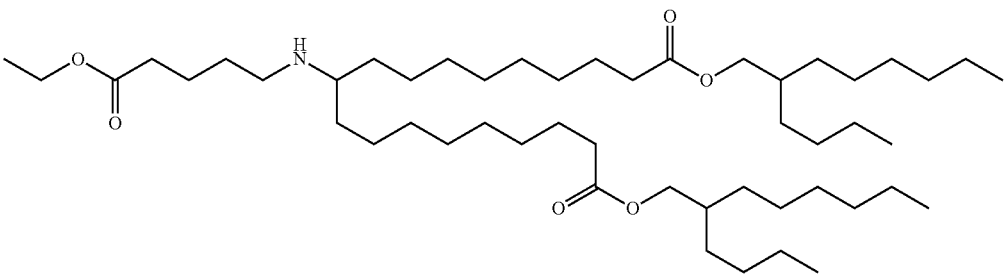 [SMILES: CCCCCCC(CCCC)COC(=O)CCCCCCCCC(CCCCCCCCC(=O)OCC(CCCC)CCCCCC)NCCCCC(=O)OCC] |
| 9 | 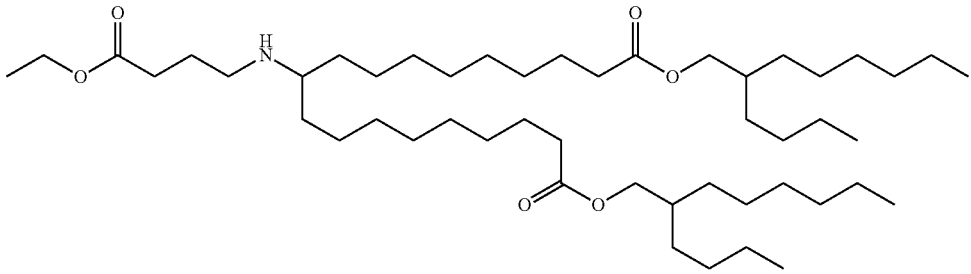 [SMILES: CCCCCCC(CCCC)COC(=O)CCCCCCCCC(CCCCCCCCC(=O)OCC(CCCC)CCCCCC)NCCCC(=O)OCC] |
| 10 | 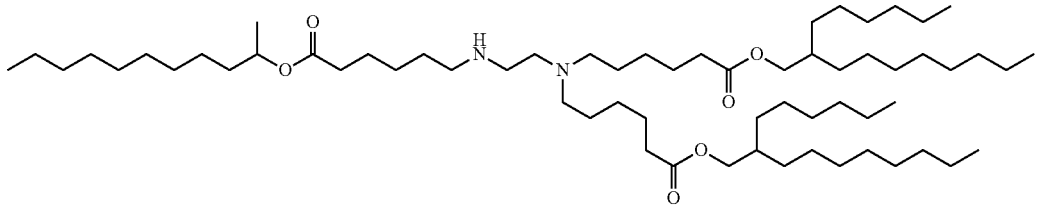 [SMILES: CCCCCCCCCC(C)OC(=O)CCCCCNCCN(CCCCCC(=O)OCC(CCCCCC)CCCCCCCC)CCCCCC(=O)OCC(CCCCCC)CCCCCCCC] |
| 11 | 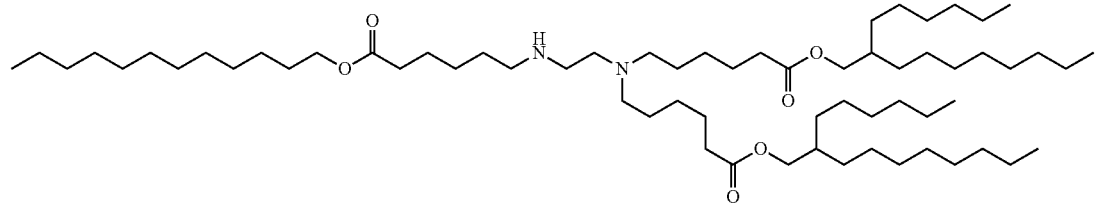 [SMILES: CCCCCCCCCCCCOC(=O)CCCCCNCCN(CCCCCC(=O)OCC(CCCCCC)CCCCCCCC)CCCCCC(=O)OCC(CCCCCC)CCCCCCCC] |
| 12 | 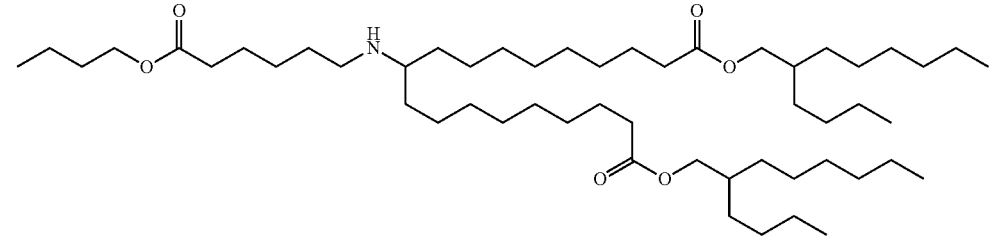 [SMILES: CCCCCCC(CCCC)COC(=O)CCCCCCCCC(CCCCCCCCC(=O)OCC(CCCC)CCCCCC)NCCCCCC(=O)OCCCC] |

The compounds in Table 1 were prepared and tested according to methods known in the art, for example those general methods described herein below.

It is understood that any embodiment of the compounds of structure (I), as set forth above, and any specific substituent and/or variable in the compound structure (I), as set forth above, may be independently combined with other embodiments and/or substituents and/or variables of compounds of structure (I) to form embodiments of the inventions not specifically set forth above. In addition, in the event that a list of substituents and/or variables is listed for any particular R group, L group or G group in a particular embodiment and/or claim, it is understood that each individual substituent and/or variable may be deleted from the particular embodiment and/or claim and that the remaining list of substituents and/or variables will be considered to be within the scope of embodiments of the invention.

It is understood that in the present description, combinations of substituents and/or variables of the depicted formulae are permissible only if such contributions result in stable compounds.

In some embodiments, compositions comprising any one or more of the compounds of structure (I) and a therapeutic agent are provided. In some embodiments are provided a lipid nanoparticle comprising one or more compounds of structure (I). For example, in some embodiments, the compositions comprise any of the compounds of structure (I) and a therapeutic agent and one or more excipient selected from neutral lipids, steroids and polymer conjugated lipids. Other pharmaceutically acceptable excipients and/or carriers are also included in various embodiments of the compositions.

In some embodiments, the neutral lipid is selected from DSPC, DPPC, DMPC, DOPC, POPC, DOPE and SM. In some embodiments, the neutral lipid is DSPC. In various embodiments, the molar ratio of the compound to the neutral lipid ranges from about 2:1 to about 8:1.

In various embodiments, the compositions further comprise a steroid or steroid analogue. In certain embodiments, the steroid or steroid analogue is cholesterol. In some of these embodiments, the molar ratio of the compound to cholesterol ranges from about 5:1 to 1:1.

In various embodiments, the polymer conjugated lipid is a pegylated lipid. For example, some embodiments include a pegylated diacylglycerol (PEG-DAG) such as 1-(monomethoxy-polyethyleneglycol)-2,3-dimyristoylglycerol (PEG-DMG), a pegylated phosphatidylethanoloamine (PEG-PE), a PEG succinate diacylglycerol (PEG-S-DAG) such as 4-O-(2',3'-di(tetradecanoyloxy)propyl-1-O-(ω-methoxy (polyethoxy)ethyl)butanedioate (PEG-S-DMG), a pegylated ceramide (PEG-cer), or a PEG dialkoxypropylcarbamate such as ω-methoxy(polyethoxy)ethyl-N-(2,3-di(tetradecanoxy)propyl)carbamate or 2,3-di(tetradecanoxy)propyl-N-(ω-methoxy(polyethoxy)ethyl)carbamate. In various embodiments, the molar ratio of the compound to the pegylated lipid ranges from about 100:1 to about 20:1.

In some embodiments, the composition comprises a pegylated lipid having the following structure (II):

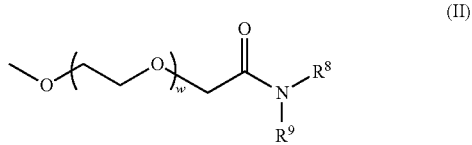

or a pharmaceutically acceptable salt, tautomer or stereoisomer thereof, wherein:

$R^8$ and $R^9$ are each independently a straight or branched, alkyl, alkenyl or alkynyl containing from 10 to 30 carbon atoms, wherein the alkyl, alkenyl or alkynyl is optionally interrupted by one or more ester bonds; and w has a mean value ranging from 30 to 60.

In some embodiments, $R^8$ and $R^9$ are each independently straight alkyl containing from 12 to 16 carbon atoms. In some embodiments, w has a mean value ranging from 43 to 53. In other embodiments, the average w is about 45. In other different embodiments, the average w is about 49.

In some embodiments, lipid nanoparticles (LNPs) comprising any one or more of the compounds of structure (I) and a therapeutic agent are provided. For example, in some embodiments, the LNPs comprise any of the compounds of structure (I) and a therapeutic agent and one or more excipient selected from neutral lipids, steroids and polymer conjugated lipids.

In some embodiments of the LNPs, the neutral lipid is selected from DSPC, DPPC, DMPC, DOPC, POPC, DOPE and SM. In some embodiments, the neutral lipid is DSPC. In various embodiments, the molar ratio of the compound to the neutral lipid ranges from about 2:1 to about 8:1.

In various embodiments of the LNPs, the compositions further comprise a steroid or steroid analogue. In certain embodiments, the steroid or steroid analogue is cholesterol. In some of these embodiments, the molar ratio of the compound to cholesterol ranges from about 5:1 to 1:1.

In various embodiments of the LNPs, the polymer conjugated lipid is a pegylated lipid. For example, some embodiments include a pegylated diacylglycerol (PEG-DAG) such as 1-(monomethoxy-polyethyleneglycol)-2,3-dimyristoylglycerol (PEG-DMG), a pegylated phosphatidylethanoloamine (PEG-PE), a PEG succinate diacylglycerol (PEG-S-DAG) such as 4-O-(2',3'-di(tetradecanoyloxy)propyl-1-O-(ω-methoxy(polyethoxy)ethyl)butanedioate (PEG-S-DMG), a pegylated ceramide (PEG-cer), or a PEG dialkoxypropylcarbamate such as ω-methoxy(polyethoxy)ethyl-N-(2,3-di(tetradecanoxy)propyl)carbamate or 2,3-di(tetradecanoxy)propyl-N-(ω-methoxy(polyethoxy)ethyl)carbamate. In various embodiments, the molar ratio of the compound to the pegylated lipid ranges from about 100:1 to about 20:1.

In some embodiments, the LNPs comprise a pegylated lipid having the following structure (II):

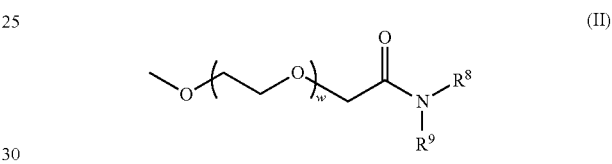

or a pharmaceutically acceptable salt, tautomer or stereoisomer thereof, wherein:

$R^8$ and $R^9$ are each independently a straight or branched, alkyl, alkenyl or alkynyl containing from 10 to 30 carbon atoms, wherein the alkyl, alkenyl or alkynyl is optionally interrupted by one or more ester bonds; and w has a mean value ranging from 30 to 60.

In some embodiments, $R^8$ and $R^9$ are each independently straight alkyl containing from 12 to 16 carbon atoms. In some embodiments, w has a mean value ranging from 43 to 53. In other embodiments, the average w is about 45. In other different embodiments, the average w is about 49.

Preparation methods for the above lipids, lipid nanoparticles and compositions are described herein below and/or known in the art, for example, in PCT Pub. No. WO 2015/199952, WO 2017/004143 and WO 2017/075531, each of which is incorporated herein by reference in their entireties.

In some embodiments of the foregoing composition, the therapeutic agent comprises a nucleic acid. For example, in some embodiments, the nucleic acid is selected from antisense and messenger RNA.

In other different embodiments, the invention is directed to a method for administering a therapeutic agent to a patient in need thereof, the method comprising preparing or providing any of the foregoing compositions and administering the composition to the patient For the purposes of administration, the compounds of structure (I) (typically in the form of lipid nanoparticles in combination with a therapeutic agent) may be administered as a raw chemical or may be formulated as pharmaceutical compositions. Pharmaceutical compositions of embodiments of the present invention comprise a compound of structure (I) (e.g., as a component in an LNP) and one or more pharmaceutically acceptable carrier, diluent or excipient. The compound of structure (I) is present in the composition in an amount which is effective to form a lipid nanoparticle and deliver the therapeutic agent, e.g., for treating a particular disease or condition of interest. Appropriate concentrations and dosages can be readily determined by one skilled in the art.

Administration of the compositions and/or LNPs of embodiments of the invention can be carried out via any of the accepted modes of administration of agents for serving similar utilities. The pharmaceutical compositions of embodiments of the invention may be formulated into preparations in solid, semi-solid, liquid or gaseous forms, such as tablets, capsules, powders, granules, ointments, solutions, suspensions, suppositories, injections, inhalants, gels, microspheres, and aerosols. Typical routes of administering such pharmaceutical compositions include, without limitation, oral, topical, transdermal, inhalation, peritoneal, sublingual, buccal, rectal, vaginal, and intranasal. The term peritoneal as used herein includes subcutaneous injections, intravenous, intramuscular, intradermal, intrasternal injection or infusion techniques. Pharmaceutical compositions of the invention are formulated so as to allow the active ingredients contained therein to be bioavailable upon administration of the composition to a patient. Compositions that will be administered to a subject or patient take the form of one or more dosage units, where for example, a tablet may be a single dosage unit, and a container of a compound of structure (I) in aerosol form may hold a plurality of dosage units. Actual methods of preparing such dosage forms are known, or will be apparent, to those skilled in this art; for example, see *Remington; The Science and Practice of Pharmacy*, 20th Edition (Philadelphia College of Pharmacy and Science, 2000). The composition to be administered will, in any event, contain a therapeutically effective amount of a compound of structure (I), or a pharmaceutically acceptable salt thereof, for treatment of a disease or condition of interest in accordance with the teachings of embodiments of this invention.

A pharmaceutical composition of embodiments of the invention may be in the form of a solid or liquid. In one aspect, the carrier(s) are particulate, so that the compositions are, for example, in tablet or powder form. The carrier(s) may be liquid, with the compositions being, for example, oral syrup, injectable liquid or an aerosol, which is useful in, for example, inhalatory administration.

When intended for oral administration, the pharmaceutical composition is preferably in either solid or liquid form, where semi-solid, semi-liquid, suspension and gel forms are included within the forms considered herein as either solid or liquid.

As a solid composition for oral administration, the pharmaceutical composition may be formulated into a powder, granule, compressed tablet, pill, capsule, chewing gum, wafer or the like form. Such a solid composition will typically contain one or more inert diluents or edible carriers. In addition, one or more of the following may be present: binders such as carboxymethylcellulose, ethyl cellulose, microcrystalline cellulose, gum tragacanth or gelatin; excipients such as starch, lactose or dextrins, disintegrating agents such as alginic acid, sodium alginate, Primogel, corn starch and the like; lubricants such as magnesium stearate or Sterotex; glidants such as colloidal silicon dioxide; sweetening agents such as sucrose or saccharin; a flavoring agent such as peppermint, methyl salicylate or orange flavoring; and a coloring agent.

When the pharmaceutical composition is in the form of a capsule, for example, a gelatin capsule, it may contain, in addition to materials of the above type, a liquid carrier such as polyethylene glycol or oil.

The pharmaceutical composition may be in the form of a liquid, for example, an elixir, syrup, solution, emulsion or suspension. The liquid may be for oral administration or for delivery by injection, as two examples. When intended for oral administration, preferred composition contain, in addition to the present compounds or LNPs, one or more of a sweetening agent, preservatives, dye/colorant and flavor enhancer. In a composition intended to be administered by injection, one or more of a surfactant, preservative, wetting agent, dispersing agent, suspending agent, buffer, stabilizer and isotonic agent may be included.

The liquid pharmaceutical compositions of embodiments of the invention, whether they be solutions, suspensions or other like form, may include one or more of the following adjuvants: sterile diluents such as water for injection, saline solution, preferably physiological saline, Ringer's solution, isotonic sodium chloride, fixed oils such as synthetic mono or diglycerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose; agents to act as cryoprotectants such as sucrose or trehalose. The peritoneal preparation can be enclosed in ampoules, disposable syringes or multiple dose vials made of glass or plastic. Physiological saline is a preferred adjuvant. An injectable pharmaceutical composition is preferably sterile.

A liquid pharmaceutical composition of embodiments of the invention intended for either peritoneal or oral administration should contain an amount of a compound of structure (I) such that a suitable LNP will be obtained.

The pharmaceutical composition of embodiments of the invention may be intended for topical administration, in which case the carrier may suitably comprise a solution, emulsion, ointment or gel base. The base, for example, may comprise one or more of the following: petrolatum, lanolin, polyethylene glycols, bee wax, mineral oil, diluents such as water and alcohol, and emulsifiers and stabilizers. Thickening agents may be present in a pharmaceutical composition for topical administration. If intended for transdermal administration, the composition may include a transdermal patch or iontophoresis device.

The pharmaceutical composition of embodiments of the invention may be intended for rectal administration, in the form, for example, of a suppository, which will melt in the rectum and release the drug. The composition for rectal administration may contain an oleaginous base as a suitable nonirritating excipient. Such bases include, without limitation, lanolin, cocoa butter and polyethylene glycol.

The pharmaceutical composition of embodiments of the invention may include various materials, which modify the physical form of a solid or liquid dosage unit. For example, the composition may include materials that form a coating shell around the active ingredients. The materials that form the coating shell are typically inert, and may be selected from, for example, sugar, shellac, and other enteric coating agents. Alternatively, the active ingredients may be encased in a gelatin capsule.

The pharmaceutical composition of embodiments of the invention in solid or liquid form may include an agent that binds to the compound of structure (I) and thereby assists in the delivery of the compound. Suitable agents that may act in this capacity include a monoclonal or polyclonal antibody, or a protein.

The pharmaceutical composition of embodiments of the invention may consist of dosage units that can be administered as an aerosol. The term aerosol is used to denote a variety of systems ranging from those of colloidal nature to systems consisting of pressurized packages. Delivery may be by a liquefied or compressed gas or by a suitable pump system that dispenses the active ingredients. Aerosols of compounds of structure (I) may be delivered in single phase, bi-phasic, or tri-phasic systems in order to deliver the active ingredient(s). Delivery of the aerosol includes the necessary container, activators, valves, sub-containers, and the like, which together may form a kit. One skilled in the art, without undue experimentation may determine preferred aerosols.

The pharmaceutical compositions of embodiments of the invention may be prepared by methodology well known in the pharmaceutical art. For example, a pharmaceutical composition intended to be administered by injection can be prepared by combining the lipid nanoparticles of the invention with sterile, distilled water or other carrier so as to form a solution. A surfactant may be added to facilitate the formation of a homogeneous solution or suspension. Surfactants are compounds that non-covalently interact with the compound of structure (I) so as to facilitate dissolution or homogeneous suspension of the compound in the aqueous delivery system.

The compositions of embodiments of the invention, or their pharmaceutically acceptable salts, are administered in a therapeutically effective amount, which will vary depending upon a variety of factors including the activity of the specific therapeutic agent employed; the metabolic stability and length of action of the therapeutic agent; the age, body weight, general health, sex, and diet of the patient; the mode and time of administration; the rate of excretion; the drug combination; the severity of the particular disorder or condition; and the subject undergoing therapy.

Compositions of embodiments of the invention may also be administered simultaneously with, prior to, or after administration of one or more other therapeutic agents. Such combination therapy includes administration of a single pharmaceutical dosage formulation of a composition of embodiments of the invention and one or more additional active agents, as well as administration of the composition of the invention and each active agent in its own separate pharmaceutical dosage formulation. For example, a composition of embodiments of the invention and the other active agent can be administered to the patient together in a single oral dosage composition such as a tablet or capsule, or each agent administered in separate oral dosage formulations. Where separate dosage formulations are used, the compounds of structure (I) and one or more additional active agents can be administered at essentially the same time, i.e., concurrently, or at separately staggered times, i.e., sequentially; combination therapy is understood to include all these regimens.

Preparation methods for the above compounds and compositions are described herein below and/or known in the art.

It will be appreciated by those skilled in the art that in the process described herein the functional groups of intermediate compounds may need to be protected by suitable protecting groups. Such functional groups include hydroxy, amino, mercapto and carboxylic acid. Suitable protecting groups for hydroxy include trialkylsilyl or diarylalkylsilyl (for example, t-butyldimethylsilyl, t-butyldiphenylsilyl or trimethylsilyl), tetrahydropyranyl, benzyl, and the like. Suitable protecting groups for amino, amidino and guanidino include t-butoxycarbonyl, benzyloxycarbonyl, and the like. Suitable protecting groups for mercapto include —C(O)—R" (where R" is alkyl, aryl or arylalkyl), p-methoxybenzyl, trityl and the like. Suitable protecting groups for carboxylic acid include alkyl, aryl or arylalkyl esters. Protecting groups may be added or removed in accordance with standard techniques, which are known to one skilled in the art and as described herein. The use of protecting groups is described in detail in Green, T. W. and P. G. M. Wutz, *Protective Groups in Organic Synthesis* (1999), 3rd Ed., Wiley. As one of skill in the art would appreciate, the protecting group may also be a polymer resin such as a Wang resin, Rink resin or a 2-chlorotrityl-chloride resin.

It will also be appreciated by those skilled in the art, although such protected derivatives of compounds of this invention may not possess pharmacological activity as such, they may be administered to a mammal and thereafter metabolized in the body to form compounds of structure (I) which are pharmacologically active. Such derivatives may therefore be described as "prodrugs". All prodrugs of compounds of structure (I) are included within the scope of embodiments of the invention.

Furthermore, all compounds of structure (I) which exist in free base or acid form can be converted to their pharmaceutically acceptable salts by treatment with the appropriate inorganic or organic base or acid by methods known to one skilled in the art. Salts of the compounds of structure (I) can be converted to their free base or acid form by standard techniques.

The compounds of structure (I), and lipid nanoparticles comprising the same, can be prepared according to methods known or derivable by one of ordinary skill in the art, for example methods analogous to those disclosed in PCT Pub. No. WO 2015/199952, WO 2017/004143 and WO 2017/075531, each of which is incorporated herein by reference in their entireties.

The following General Reaction Schemes illustrate exemplary methods to make compounds of structure (I):

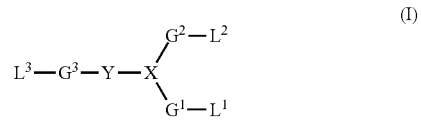

(I)

or a pharmaceutically acceptable salt, tautomer or stereoisomer thereof, wherein X, Y, $L^1$, $L^2$, $L^3$, $G^1$, $G^2$ and $G^3$ are as defined herein. It is understood that one skilled in the art may be able to make these compounds by similar methods or by combining other methods known to one skilled in the art. It is also understood that one skilled in the art would be able to make, in a similar manner as described below, other compounds of structure (I) not specifically illustrated below by using the appropriate starting components and modifying the parameters of the synthesis as needed. In general, starting components may be obtained from sources such as Sigma Aldrich, Lancaster Synthesis, Inc., Maybridge, Matrix Scientific, TCI, and Fluorochem USA, etc. or synthesized according to sources known to those skilled in the art (see, for example, Advanced Organic Chemistry: Reactions, Mechanisms, and Structure, 5th edition (Wiley, December 2000)) or prepared as described in this invention.

GENERAL REACTION SCHEME 1

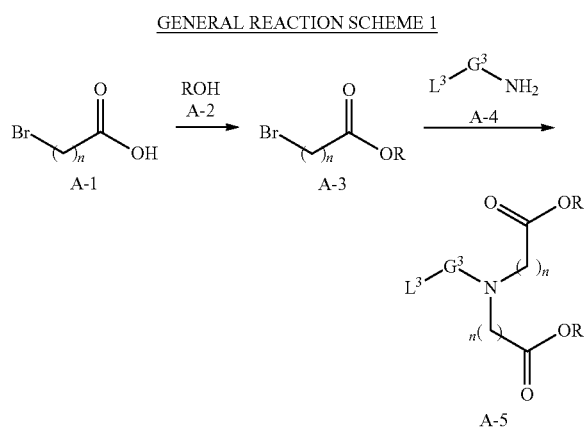

Embodiments of the compound of structure (I) (e.g., compound A-5) can be prepared according to General Reaction Scheme 1 ("Method A"), wherein each R independently represents $R^1$ or $R^2$, and each n is independently an integer from 2 to 12. Referring to General Reaction Scheme 1, compounds of structure A-1 can be purchased from commercial sources or prepared according to methods familiar to one of ordinary skill in the art. A mixture of A-1, A-2 and DMAP is treated with DCC to give the bromide A-3. A mixture of the bromide A-3, a base (e.g., N,N-diisopropylethylamine) and A-4 is heated at a temperature and time sufficient to produce A-5 after any necessary workup and or purification step. Protecting group strategies or alternative order of synthetic steps may be employed to avoid unwanted side reactions with the $L^3$ moiety as needed.

GENERAL REACTION SCHEME 2

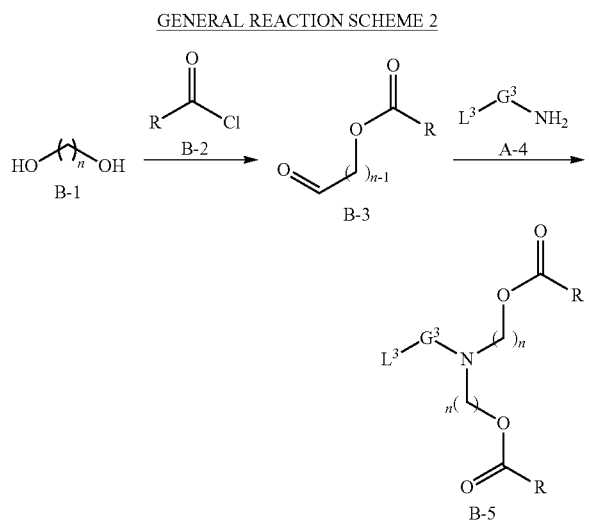

Embodiments of the compound of structure (I) (e.g., compound B-5) can be prepared according to General Reaction Scheme 2 ("Method B"), wherein each R independently represents $R^1$ or $R^2$, and each n is independently an integer from 2 to 12. As shown in General Reaction Scheme 2, compounds of structure B-1 can be purchased from commercial sources or prepared according to methods familiar to one of ordinary skill in the art. A solution of B-1 (1 equivalent) is treated with acid chloride B-2 (1 equivalent) and a base (e.g., triethylamine). The crude product is treated with an oxidizing agent (e.g., pyridinium chlorochromate) and intermediate product B-3 is recovered. A solution of crude B-3, an acid (e.g., acetic acid), and A-4 is then treated with a reducing agent (e.g., sodium triacetoxyborohydride) to obtain B-5 after any necessary work up and/or purification. Protecting group strategies or alternative order of synthetic steps may be employed to avoid unwanted side reactions with the L moiety as needed.

GENERAL REACTION SCHEME 3

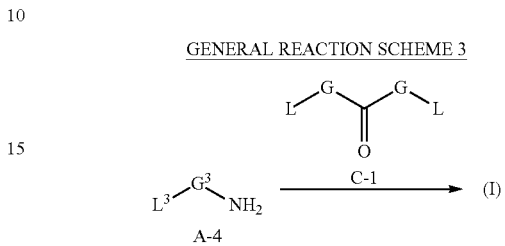

Embodiments of the compound of structure (I) can be prepared according to General Reaction Scheme 3 ("Method C"), wherein each G independently represents $G^1$, $G^{1'}$, $G^2$ or $G^{2'}$, and each L independently represents $L^1$, $L^{1'}$, $L^2$ or $L^{2'}$. Referring to General Reaction Scheme 1, compounds of structure A-4 and C-1 can be purchased from commercial sources or prepared according to methods familiar to one of ordinary skill in the art. A solution of A-4 and C-1 is treated with a reducing agent (e.g., sodium triacetoxyborohydride) to obtain a compound of structure (I) after any necessary work up.

It should be noted that although starting materials A-1 and B-1 are depicted above as including only saturated methylene carbons, starting materials which include carbon-carbon double bonds may also be employed for preparation of compounds which include carbon-carbon double bonds.

It should be noted that various alternative strategies for preparation of compounds of structure (I) are available to those of ordinary skill in the art. For example, certain moieties may include a substituent, such as hydroxyl, and appropriate protecting groups may be required to mask the substituent, or the substituent may be added at a different point in the synthesis to avoid unwanted side reactions. The use of protecting groups as needed and other modification to the above General Reaction Schemes 1-3 will be readily apparent to one of ordinary skill in the art. The following examples are provided for purpose of illustration and not limitation.

Example 1

Luciferase mRNA In Vivo Evaluation Using Lipid Nanoparticle Compositions

A lipid of structure (I), DSPC, cholesterol and PEG-lipid were solubilized in ethanol at a molar ratio of 50:10:38.5:1.5 or 47.5:10:40.8:1.7. Lipid nanoparticles (LNP) were prepared at a total lipid to mRNA weight ratio of approximately 10:1 to 30:1. Briefly, the mRNA was diluted to 0.2 mg/mL in 10 to 50 mM citrate buffer, pH 4. Syringe pumps were used to mix the ethanolic lipid solution with the mRNA aqueous solution at a ratio of about 1:5 to 1:3 (vol/vol) with total flow rates above 15 mL/min. The ethanol was then removed and the external buffer replaced with PBS by dialysis. Finally, the lipid nanoparticles were filtered through a 0.2 µm pore sterile filter.

Studies were performed in 6-8 week old female $C_{57}BL/6$ mice (Charles River) 8-10 week old CD-1 (Harlan) mice (Charles River) according to guidelines established by an institutional animal care committee (ACC) and the Canadian Council on Animal Care (CCAC). Varying doses of mRNA-lipid nanoparticle were systemically administered by tail vein injection and animals euthanized at a specific time point (e.g., 4 hours) post-administration. Liver and spleen were collected in pre-weighed tubes, weights determined, immediately snap frozen in liquid nitrogen and stored at −80° C. until processing for analysis.

For liver, approximately 50 mg was dissected for analyses in a 2 mL FastPrep tubes (MP Biomedicals, Solon Ohio). ¼" ceramic sphere (MP Biomedicals) was added to each tube and 500 µL of Glo Lysis Buffer—GLB (Promega, Madison Wis.) equilibrated to room temperature was added to liver tissue. Liver tissues were homogenized with the FastPrep24 instrument (MP Biomedicals) at 2×6.0 m/s for 15 seconds. Homogenate was incubated at room temperature for 5 minutes prior to a 1:4 dilution in GLB and assessed using SteadyGlo Luciferase assay system (Promega). Specifically, 50 µL of diluted tissue homogenate was reacted with 50 µL of SteadyGlo substrate, shaken for 10 seconds followed by 5 minute incubation and then quantitated using a $CentroXS^3$ LB 960 luminometer (Berthold Technologies, Germany). The amount of protein assayed was determined by using the BCA protein assay kit (Pierce, Rockford, Ill.). Relative luminescence units (RLU) were then normalized to total µg protein assayed. To convert RLU to ng luciferase a standard curve was generated with QuantiLum Recombinant Luciferase (Promega).

The FLuc mRNA (L-6107 or L-7602) from Trilink Biotechnologies will express a luciferase protein, originally isolated from the firefly, *Photinus pyralis*. FLuc is commonly used in mammalian cell culture to measure both gene expression and cell viability. It emits bioluminescence in the presence of the substrate, luciferin. This capped and polyadenylated mRNA is fully substituted with 5-methylcytidine and pseudouridine.

Example 2

Determination of $Pk_A$ of Formulated Lipids

As described elsewhere, the pKa of formulated lipids is correlated with the effectiveness of LNPs for delivery of nucleic acids (see Jayaraman et al, Angewandte Chemie, International Edition (2012), 51(34), 8529-8533; Semple et al, Nature Biotechnology 28, 172-176 (2010)). In some embodiments, the preferred range of pKa is ~5 to ~7. The $pK_a$ of representative lipids was determined in lipid nanoparticles using an assay based on fluorescence of 2-(p-toluidino)-6-napthalene sulfonic acid (TNS). Lipid nanoparticles comprising compound of structure (I)/DSPC/cholesterol/PEG-lipid (50/10/38.5/1.5 or 47.5:10:40.8:1.7 mol %) in PBS at a concentration of 0.4 mM total lipid were prepared using the in-line process as described in Example 1. TNS was prepared as a 100 µM stock solution in distilled water. Vesicles were diluted to 24 µM lipid in 2 mL of buffered solutions containing 10 mM HEPES, 10 mM MES, 10 mM ammonium acetate, and 130 mM NaCl, where the pH ranged from 2.5 to 11. An aliquot of the TNS solution was added to give a final concentration of 1 µM and following vortex mixing fluorescence intensity was measured at room temperature in a SLM Aminco Series 2 Luminescence Spectrophotometer using excitation and emission wavelengths of 321 nm and 445 nm. A sigmoidal best fit analysis was applied to the fluorescence data and the $pK_a$ was measured as the pH giving rise to half-maximal fluorescence intensity.

Lipid nanoparticle particle size was approximately 55-95 nm diameter, and in some instances approximately 70-90 nm diameter as determined by quasi-elastic light scattering using a Malvern Zetasizer Nano ZS (Malvern, UK). The diameters given are intensity weighted means. Encapsulation was determined using a fluorescent intercalating dye based assay (Ribogreen).

Compounds of structure (I) were formulated using the following molar ratio: 47.5% cationic lipid/10% distearoylphosphatidylcholine (DSPC)/40.8% Cholesterol/1.7% PEG lipid ("PEG-DMA" 2-[2-(ω-methoxy (polyethyleneglycol$_{2000}$)ethoxy]-N,N-ditetradecylacetamide). Relative activity was determined by measuring luciferase expression in the liver 4 hours following administration via tail vein injection as described in Example 1.

Example 3

Determination of Efficacy of Lipid Nanoparticle Formulations Containing Various Cationic Lipids Using an In Vivo Luciferase mRNA Expression Rodent Model The cationic lipids shown in Table 2 have previously been tested with nucleic acids. For comparative purposes, these lipids were also used to formulate lipid nanoparticles containing the FLuc mRNA (L-6107) using an in line mixing method, as described in Example 1 and in PCT/US10/22614, which is hereby incorporated by reference in its entirety. Lipid nanoparticles may be formulated using the following molar ratio: 50% Cationic lipid/10% distearoylphosphatidylcholine (DSPC)/38.5% Cholesterol/1.5% PEG lipid ("PEG-DMG", i.e., 1-(monomethoxy-polyethyleneglycol)-2,3-dimyristoylglycerol, with an average PEG molecular weight of 2000). In alternate embodiments, cationic lipid, DSPC, cholesterol and PEG-lipid are formulated at a molar ratio of approximately 47.5:10:40.8:1.7. Relative activity was determined by measuring luciferase expression in the liver 4 hours following administration via tail vein injection as described in Example 1. The activity was compared at a dose of 0.3 and 1.0 mg mRNA/kg and expressed as ng luciferase/g liver measured 4 hours after administration, as described in Example 1.

TABLE 2

Comparator Lipids showing activity with mRNA

| Compound | Liver Luc @ 0.3 mg/kg dose | Liver Luc @ 1.0 mg/kg dose | Structure |
|---|---|---|---|
| MC2 | 4 ± 1 | N/D | 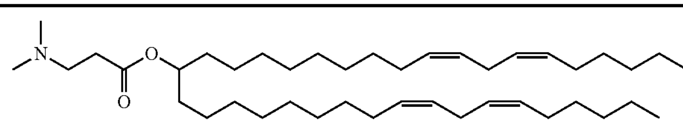 |

TABLE 2-continued

Comparator Lipids showing activity with mRNA

| Compound | Liver Luc @ 0.3 mg/kg dose | Liver Luc @ 1.0 mg/kg dose | Structure |
|---|---|---|---|
| DLinDMA | 13 ± 3 | 67 ± 20 | 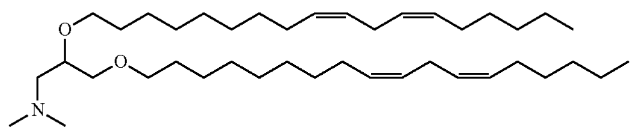 [SMILES: CCCCC/C=C\C/C=C\CCCCCCCCOCC(CN(C)C)OCCCCCCCC/C=C\C/C=C\CCCCC] |
| MC4 | 41 ± 10 | N/D | 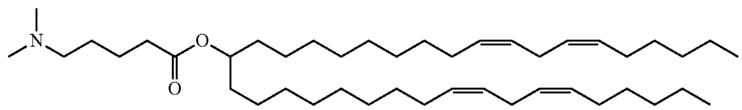 [SMILES: CCCCC/C=C\C/C=C\CCCCCCCCC(CCCCCCCC/C=C\C/C=C\CCCCC)OC(=O)CCCCN(C)C] |
| XTC2 | 80 ± 28 | 237 ± 99 | 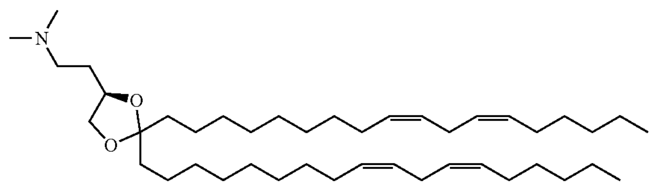 [SMILES: CCCCC/C=C\C/C=C\CCCCCCCCC1(CCCCCCCC/C=C\C/C=C\CCCCC)OC[C@@H](CCN(C)C)O1] |
| MC3 | 198 ± 126 | 757 ± 528 | 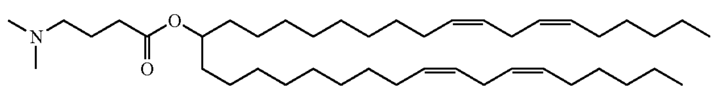 [SMILES: CCCCC/C=C\C/C=C\CCCCCCCCC(CCCCCCCC/C=C\C/C=C\CCCCC)OC(=O)CCCN(C)C] |
| 319 (2% PEG) | 258 ± 67 | 681 ± 203 | 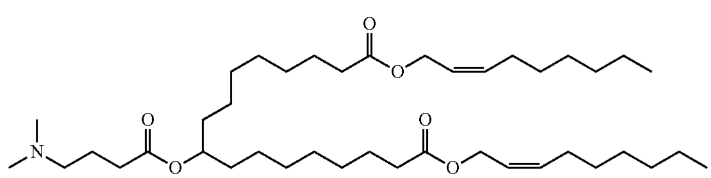 [SMILES: CCCCCC/C=C\COC(=O)CCCCCCCC(CCCCCCCC(=O)OC/C=C\CCCCCC)OC(=O)CCCN(C)C] |
| 137 | 281 ± 203 | 588 ± 303 | 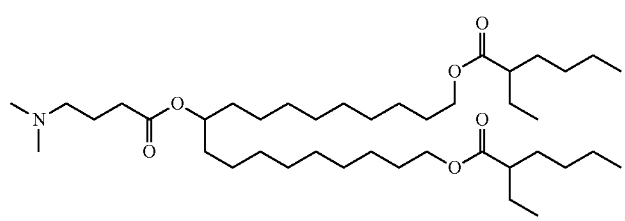 [SMILES: CCCCC(CC)C(=O)OCCCCCCCCCC(CCCCCCCCCOC(=O)C(CC)CCCC)OC(=O)CCCN(C)C] |
| A | 77 ± 40 | 203 ± 122 | 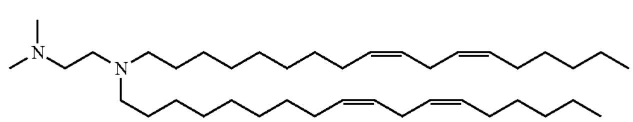 [SMILES: CCCCC/C=C\C/C=C\CCCCCCCCN(CCCCCCCC/C=C\C/C=C\CCCCC)CCN(C)C] |

Representative compounds of the invention shown in Table 3 were formulated using the following molar ratio: 50% cationic lipid/10% distearoylphosphatidylcholine (DSPC)/38.5% Cholesterol/1.5% PEG lipid ("PEG-DMA" 2-[2-(ω-methoxy(polyethyleneglycol$_{2000}$)ethoxy]-N,N-ditetradecylacetamide) or 47.5% cationic lipid/10% DSPC/40.8% Cholesterol/1.7% PEG lipid. Relative activity was determined by measuring luciferase expression in the liver 4 hours following administration via tail vein injection as described in Example 1. The activity was compared at a dose of 0.5 mg mRNA/kg unless noted otherwise and expressed as ng luciferase/g liver measured 4 hours after administration, as described in Example 1. Compound numbers in Table 3 refer to the compound numbers of Table 1.

TABLE 3

Novel Cationic Lipids and Associated Activity

| Cmp. No. | pK$_a$ | Liver Luc @ 0.5 mg/kg (ng luc/ g liver) | Structure |
| --- | --- | --- | --- |
| 1 | 6.39 | 1235 ± 345* | 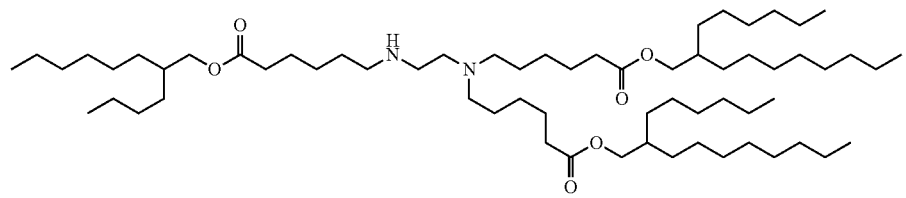 [SMILES: CCCCCCCCC(CCCCCC)COC(=O)CCCCCN(CCCCCC(=O)OCC(CCCCCC)CCCCCCCC)CCNCCCCCC(=O)OCC(CCCC)CCCCCC] |
| 2 | 5.76 | 29 ± 4 | 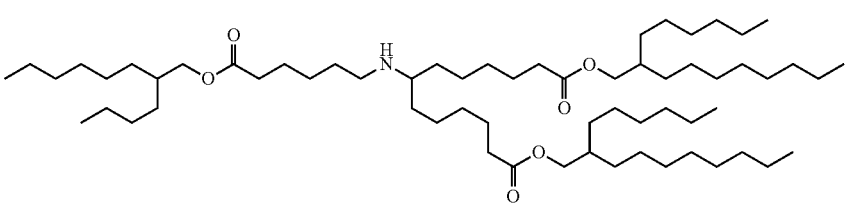 [SMILES: CCCCCCCCC(CCCCCC)COC(=O)CCCCCC(CCCCCC(=O)OCC(CCCCCC)CCCCCCCC)NCCCCCC(=O)OCC(CCCC)CCCCCC] |
| 3 | 6.50 | 33 ± 1 | 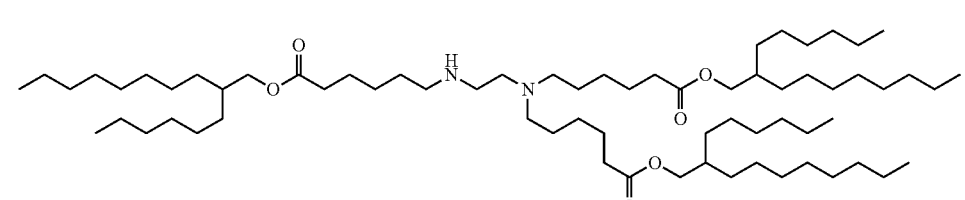 |
| 4 | 6.11 | 102 ± 42 | 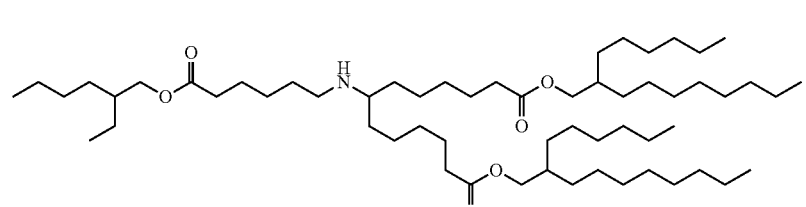 |

*dosed at 0.3 mg/kg

Example 4

Synthesis of Compound 1

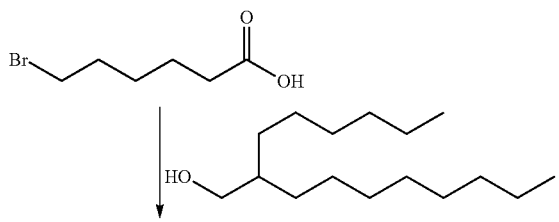

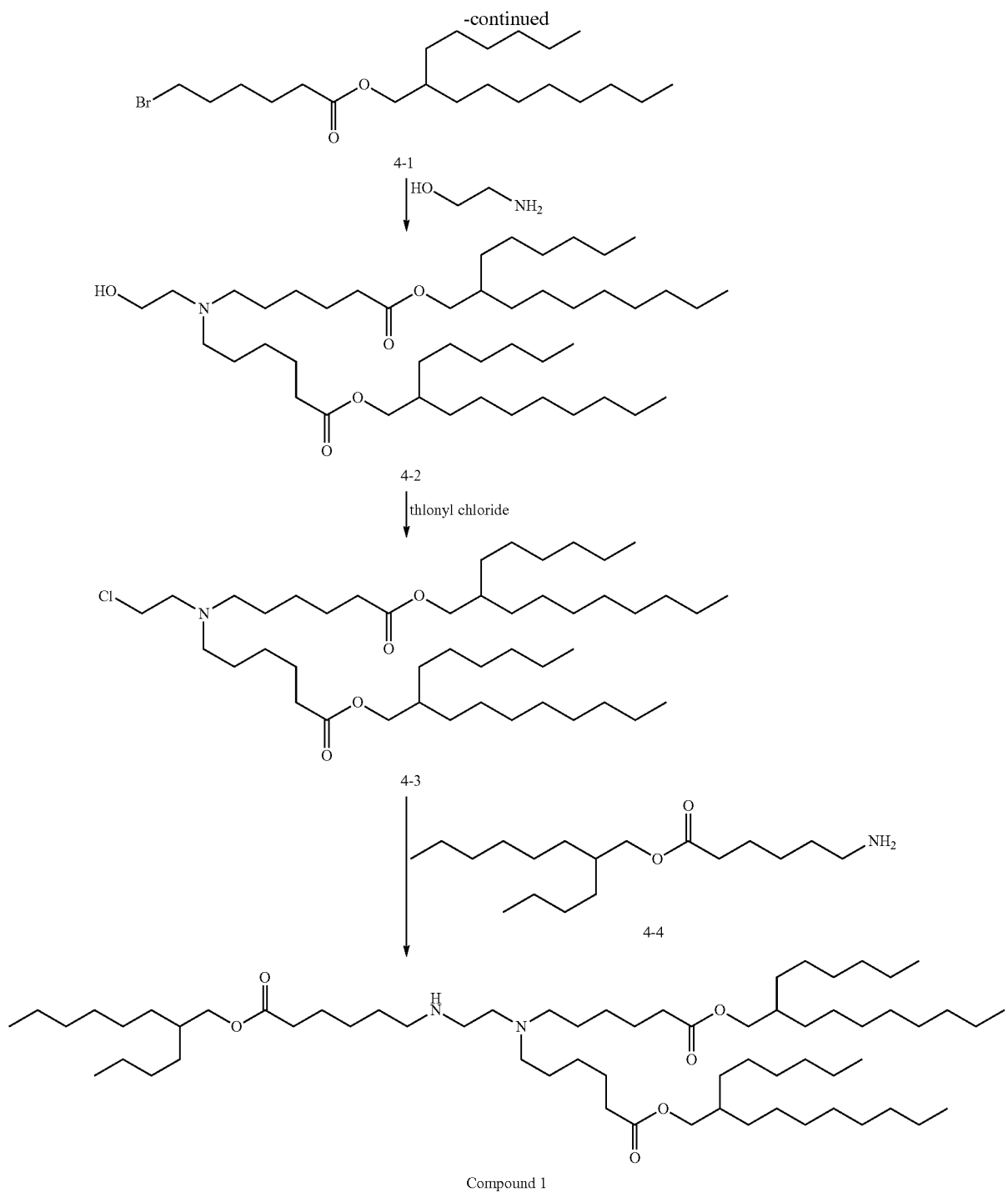

Compound 1

Synthesis of 4-1

To a solution of 6-bromohexanoic acid (16 mmol, 3.12 g), 2-hexyl-1-decanol (22.4 mmol, 5.43 g) and DMAP (8 mmol, 976 mg) in DCM (50 mL) was added DCC (17.6 mmol, 3.62 g). The resulting mixture was stirred at RT for 16 h. The precipitate (DCU) was removed by filtration. The filtrate was concentrated and the resulting residue oil/solid was purified by column chromatography on silica gel (0 to 5% ethyl acetate in hexanes). This gave the desired product as a colorless oil (5.79 g, colorless oil, 13.8 mmol, 86%).

Synthesis of 4-2

To a solution of 2-aminoethanol (333 mg, 5.46 mmol) in 35 ml of anhydrous THF were added 4-1 (4.37 g, 10.4 mmol), potassium carbonate (1.44 g, 10.4 mmol), cesium carbonate (534 mg, 1.64 mmol) and sodium iodide (30 mg). The resulting mixture in a sealed pressure flask was heated at 70 C for 6 days. The solvent was evaporated under reduced pressure and the residue was taken up in a mixture of hexane and ethyl acetate (94:4) and washed with water and brine. The organic layer was separated and dried over anhydrous sodium sulfate. The dried extract (320 mL) was loaded on a column of silica gel. The column was eluted a mixture of with Hexane, EtOAc and triethylamine (95:5:0 to 80:20:1). This gave the desired product as a colorless oil (2.68 g, 3.63 mmol, 70%). $^1$HNMR (400 MHz, CDCl$_3$) δ: 3.97 (d, 5.8 Hz, 4H), 3.53 (t, 5.3 Hz, 2H), 3.08-2.79 (br. 1H), 2.57 (t, 5.3 Hz, 2H), 2.45 (t-like, 7.4 Hz, 4H), 2.31 (t, 7.5 Hz, 4H), 1.67-1.59 (m, 6H), 1.51-1.41 (m, 4H), 1.38-1.10 (52H), 0.89 (t-like, 6.8 Hz, 12H).

Synthesis of 4-3

To an ice-cooled solution of 027-76 (2.16 g, 2.93 mmol) in 8 mL of CHCl$_3$, was added thionyl chloride (8.79 mmol, 1.05 g) in 35 mL of chloroform dropwise under an Ar atmosphere. After the addition of SOCl$_2$ (1-2 min) was complete, the ice bath was removed and the reaction mixture was stirred for 16 h at room temperature (20 C). Removal of chloroform, and SOCl$_2$ under reduced pressure gave a thick dark red oil. The crude product was purified by flash column chromatography on silica gel (0 to 1% MeOH in chloroform with trace of Et$_3$N). The desired product was obtained as brown oil (1.786 g, 2.36 mmol, 80%).

Synthesis of Compound 1

A solution of 4-3 (150 mg, 0.2 mmol), 4-4 (0.8 mmol, 240 mmol; prepared from 2-butyl-1-octanol, 6-Aminocaproic acid) and N,N-diisopropylethylamine (0.035 mL) in acetonitrile (10 mL) was sealed and was heated at 64 C overnight. The reaction mixture was cooled and concentrated. The residue was purified twice by flash dry column chromatography on silica gel (hexane-EtOAc-Et3N, 95:5:0 to 80:20:1 and MeOH in chloroform, 0 to 5%). The desired product was obtained as colorless oil (36 mg). $^1$HNMR (400 MHz, CDCl3) δ: 3.97 (d, 5.8 Hz, 6H), 2.67-2.56 (m, 4H), 2.55-2.50 (m, 2H), 2.40 (t-like, 7.5 Hz, 4H), 2.34-2.28 (m, 6H), 1.70-1.35 (m, 18H), 1.35-1.17 (m, 68H), 0.92-0.87 (m, 18H).

Example 5

Synthesis of Compound 2

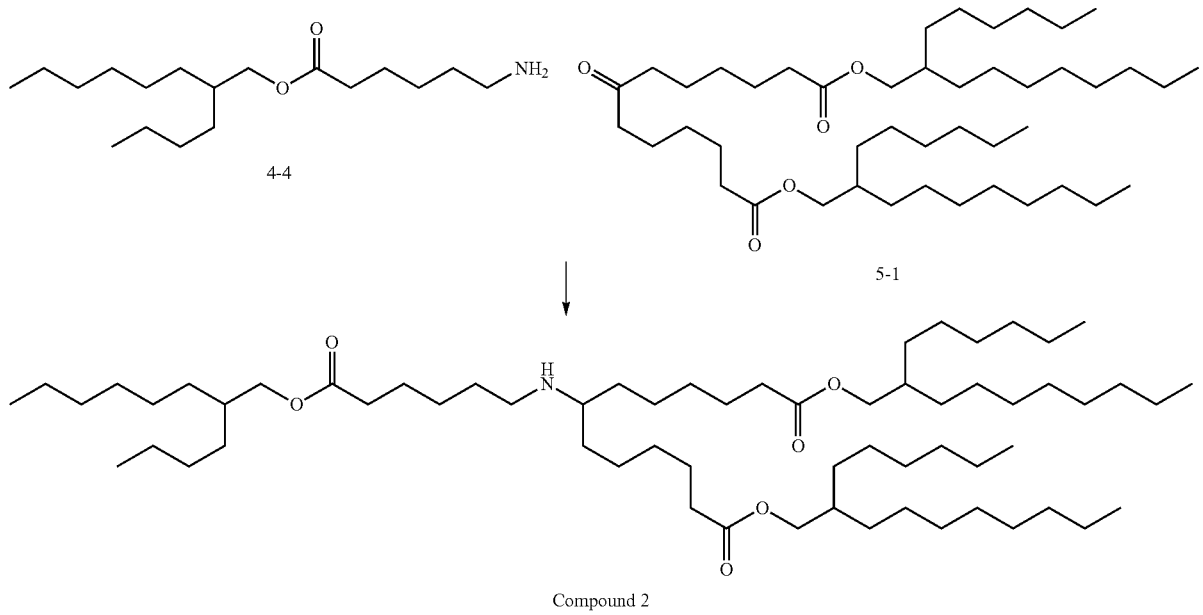

Compound 2

A solution of the ketone 5-1 (250 mg, 0.35 mmol; prepared according to the literature procedure) and the amine 4-4 (0.35 mmol, 106 mg) in DCE (5 mL) was stirred at RT under Ar for about 15 min. To the solution was added sodium triacetoxyborohydride (1.06 mmol, 222 mg) and AcOH (0.49 mmol, 29 mg). The mixture was stirred at RT under a Ar atmosphere for 7 days. The reaction mixture was concentrated and diluted with a mixture of hexanes and EtOAc (ca 19:1) and washed with dilute NaOH, sat NaHCO3 and brine. The extract was dried over sodium sulfate and filtered through a pad of silica gel. The pad was washed with a mixture of hexane-EtOAc-Et3N (80:20:1). The washing was concentrated to give the crude product. The crude product was purified by flash dry column chromatography on silica gel (MeOH in chloroform, 0 to 5%). The desired product was obtained as colorless oil (111 mg, 0.11 mmol, 32%). $^1$HNMR (400 MHz, CDCl3) δ: 3.97 (d, 5.8 Hz, 6H), 2.55 (t-like, 7.0 Hz, 2H), 2.48-2.39 (m, 1H), 2.34-2.28 (m, 6H), 1.69-1.58 (m, 8H), 1.52-1.42 (m, 3H), 1.42-1.17 (m, 78H), 0.92-0.87 (m, 18H), 0.80-0.72 (br., 1H).

Example 6

Synthesis of Compound 3

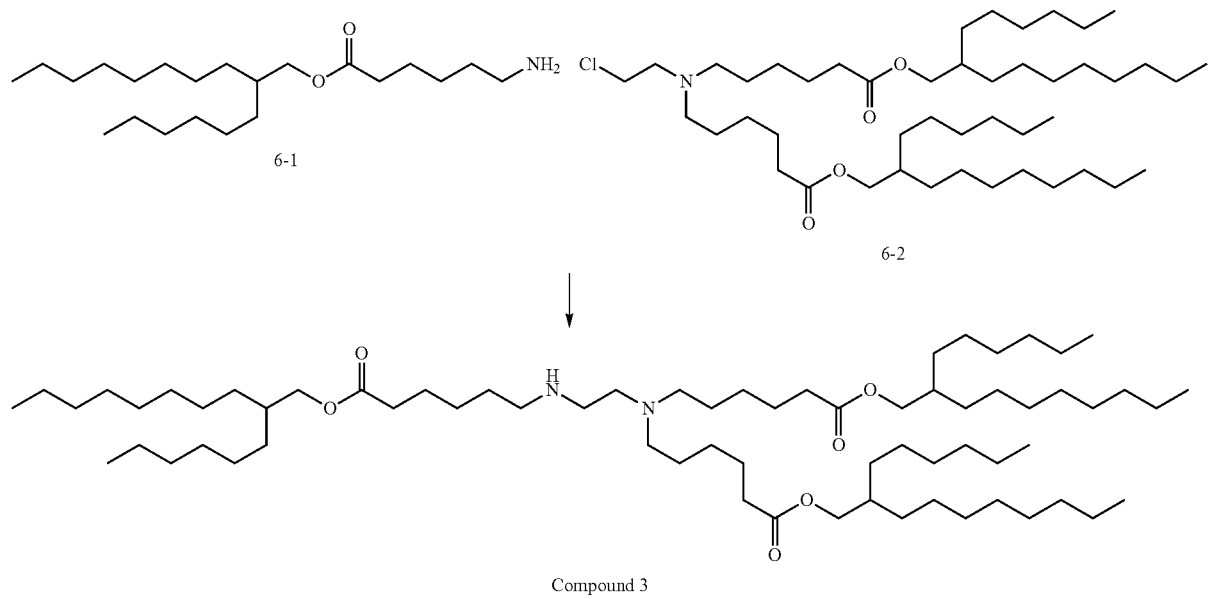

A solution of 6-2 (150 mg, 0.2 mmol), 6-1 (0.8 mmol, 284 mg; prepared from 2-hexyl-1-decanol, 6-Aminocaproic acid) and N,N-diisopropylethylamine (0.035 mL) in acetonitrile (10 mL) was sealed and was heated at 74 C overnight. The reaction mixture was cooled and concentrated. The residue was purified twice by flash dry column chromatography on silica gel (hexane-EtOAc-Et3N, 95:5:0 to 80:20:1 and MeOH in chloroform, 0 to 5%). The desired product was obtained as colorless oil (96 mg, 0.09 mmol, 45%). 1HNMR (400 MHz, CDCl3) d: 3.97 (d, 5.8 Hz, 6H), 2.67-2.56 (m, 4H), 2.55-2.50 (m, 2H), 2.40 (t-like, 7.5 Hz, 4H), 2.34-2.28 (m, 6H), 1.70-1.35 (m, 18H), 1.35-1.17 (m, 76H), 0.92-0.87 (m, 18H).

Example 7

Synthesis of Compound 4

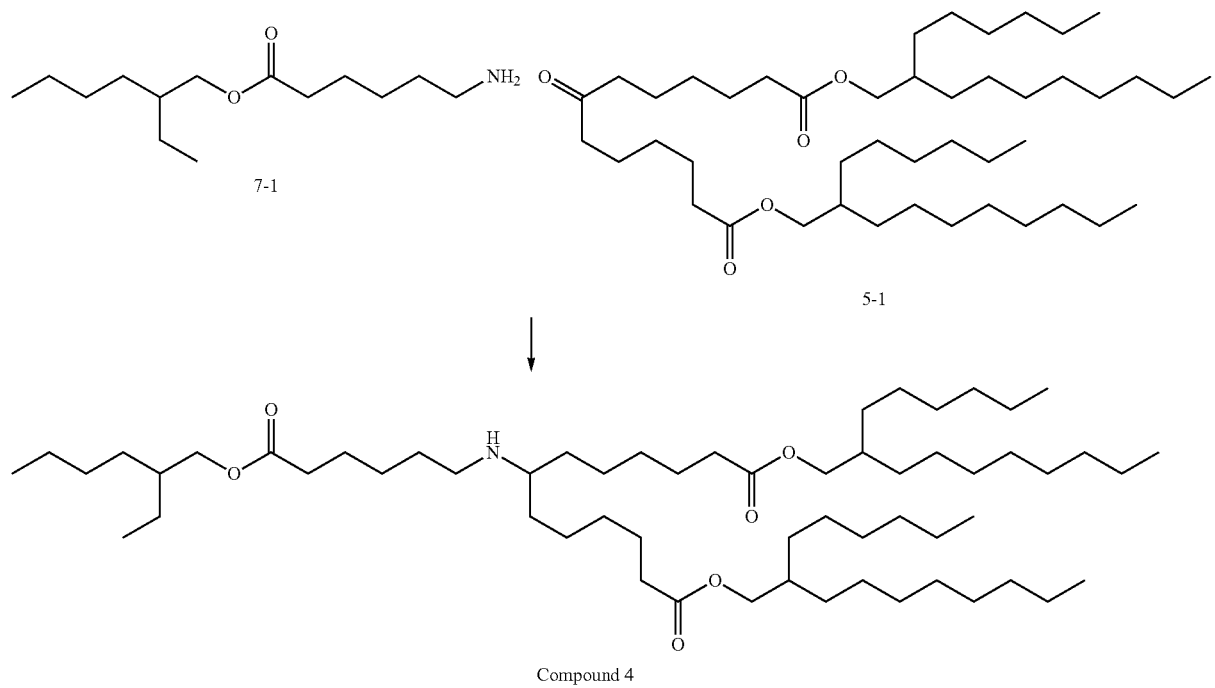

A solution of the ketone 5-1 (250 mg, 0.35 mmol; prepared according to the literature procedure) and the amine 7-1 (0.5 mmol, 122 mg; prepared from 2-ethyl-1-butanol, 6-Aminocaproic acid) in DCE (5 mL) was stirred at RT under Ar for about 15 min. To the solution was added sodium triacetoxyborohydride (1.06 mmol, 222 mg) and AcOH (0.49 mmol, 29 mg). The mixture was stirred at RT under a Ar atmosphere for 2 days. The reaction mixture was concentrated and diluted with a mixture of hexanes and EtOAc (ca 19:1) and washed with dilute NaOH, sat NaHCO3 and brine. The extract was dried over sodium sulfate and filtered through a pad of silica gel. The pad was washed with a mixture of hexane-EtOAc-Et3N (80:20:1). The washing was concentrated to give the crude product. The crude product was purified by flash dry column chromatography on silica gel (MeOH in chloroform, 0 to 5%). The desired product was obtained as colorless oil (169 mg, 0.18 mmol, 52%). 1HNMR (400 MHz, CDCl3) δ: 4.03-3.95 (m, 6H), 2.55 (t-like, 7.1 Hz, 2H), 2.44 (quintet-like, 5.4 Hz, 1H), 2.34-2.28 (m, 6H), 1.69-1.58 (m, 8H), 1.52-1.42 (m, 3H), 1.42-1.17 (m, 70H), 0.92-0.87 (m, 18H), 0.82-0.70 (br., 1H).

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet, including U.S. Provisional Patent Application No. 62/547,043, filed Aug. 17, 2017, are incorporated herein by reference, in their entirety. Aspects of the embodiments can be modified, if necessary to employ concepts of the various patents, applications and publications to provide yet further embodiments. These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A compound having the following structure (I):

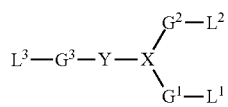

or a pharmaceutically acceptable salt, prodrug or stereoisomer thereof, wherein:

X is N, and Y is absent; or X is CR, and Y is NR;

$L^1$ is —O(C=O)$R^1$, —(C=O)O$R^1$, —C(=O)$R^1$, —O$R^1$, —S(O)$_x$$R^1$, —S—S$R^1$, —C(=O)S$R^1$, —SC(=O)$R^1$, —NR$^a$C(=O)$R^1$, —C(=O)NR$^b$R$^c$, —NR$^a$C(=O)NR$^b$R$^c$, —OC(=O)NR$^b$R$^c$ or —NR$^a$C(=O)OR$^1$;

$L^2$ is —O(C=O)$R^2$, —(C=O)O$R^2$, —C(=O)$R^2$, —O$R^2$, —S(O)$_x$$R^2$, —S—S$R^2$, —C(=O)S$R^2$, —SC(=O)$R^2$, —NR$^a$C(=O)$R^2$, —C(=O)NR$^e$R$^f$, —NR$^a$C(=O)NR$^e$R$^f$, —OC(=O)NR$^e$R$^f$, —NR$^a$C(=O)OR$^2$ or a direct bond to $R^2$;

$L^3$ is —O(C=O)$R^3$ or —(C=O)O$R^3$;

$G^1$ and $G^2$ are each independently $C_2$-$C_{12}$ alkylene or $C_2$-$C_{12}$ alkenylene;

$G^3$ is $C_1$-$C_8$ alkylene, $C_2$-$C_8$ alkenylene, $C_1$-$C_8$ heteroalkylene or $C_2$-$C_8$ heteroalkenylene when X is CR, and Y is NR; and $G^3$ is unsubstituted $C_1$-$C_8$ heteroalkylene or unsubstituted $C_2$-$C_8$ heteroalkenylene when X is N, and Y is absent;

$R^a$, $R^b$, $R^d$ and $R^e$ are each independently H or $C_1$-$C_{12}$ alkyl or $C_1$-$C_{12}$ alkenyl;

$R^c$ and $R^f$ are each independently $C_1$-$C_{12}$ alkyl or $C_2$-$C_{12}$ alkenyl;

each R is independently H or unsubstituted $C_1$-$C_{12}$ alkyl;

$R^1$, $R^2$ and $R^3$ are each independently $C_1$-$C_{24}$ alkyl or $C_2$-$C_{24}$ alkenyl; and x is 0, 1 or 2.

2. The compound of claim 1, wherein $G^3$ is $C_1$-$C_8$ alkylene.

3. The compound of claim 1, wherein $G^3$ is unsubstituted $C_1$-$C_8$ heteroalkylene.

4. The compound of claim 3, wherein $G^3$ is $C_1$-$C_8$ aminylalkylene.

5. The compound of claim 1, wherein X is N and Y is absent.

6. The compound of claim 1, wherein X is CR and Y is NR.

7. The compound of claim 1, having one of the following structures (IA), (IB), (IC) or (ID):

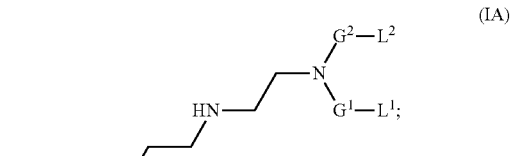

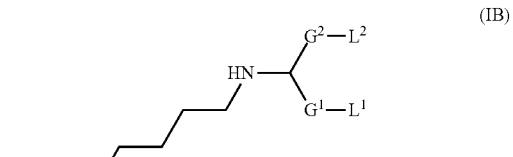

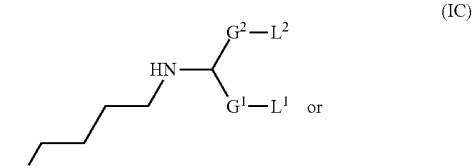

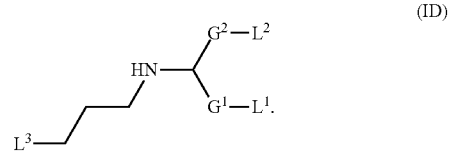

8. The compound of claim 1, wherein $L^1$ is —O(C=O)$R^1$, —(C=O)O$R^1$ or —C(=O)NR$^b$R$^c$, and $L^2$ is —O(C=O)$R^2$, —(C=O)O$R^2$ or —C(=O)NR$^e$R$^f$.

9. The compound of claim 8, wherein $L^1$ is —(C=O)O$R^1$ and $L^2$ is —(C=O)O$R^2$.

10. The compound of claim 1, wherein $L^3$ is —(C=O)OR$^3$.

11. The compound of claim 1, wherein $G^1$ and $G^2$ are each independently $C_4$-$C_{10}$ alkylene.

12. The compound of claim 1, wherein $R^1$, $R^2$ and $R^3$ are each, independently, branched $C_6$-$C_{24}$ alkyl.

13. The compound of claim 12, wherein $R^1$, $R^2$ and $R^3$ each, independently, have the following structure:

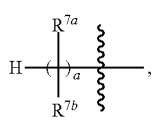

wherein:
R$^{7a}$ and R$^{7b}$ are, at each occurrence, independently H or C$_1$-C$_{12}$ alkyl; and
a is an integer from 2 to 12,
wherein R$^{7a}$, R$^{7b}$ and a are each selected such that R$^1$ and R$^2$ are each independently branched and independently comprise from 6 to 20 carbon atoms.

14. The compound of claim 13, wherein a is an integer from 8 to 12.

15. The compound of claim 13, wherein at least one occurrence of R$^{7b}$ is C$_1$-C$_8$ alkyl is methyl, ethyl, n-propyl, iso-propyl, n-butyl, iso-butyl, tert-butyl, n-hexyl or n-octyl.

16. The compound of claim 1, wherein X is CR, Y is NR and R$^3$ is C$_1$-C$_{12}$ alkyl.

17. The compound of claim 1, wherein R$^1$, R$^2$ and R$^3$ independently have one of the following structures:

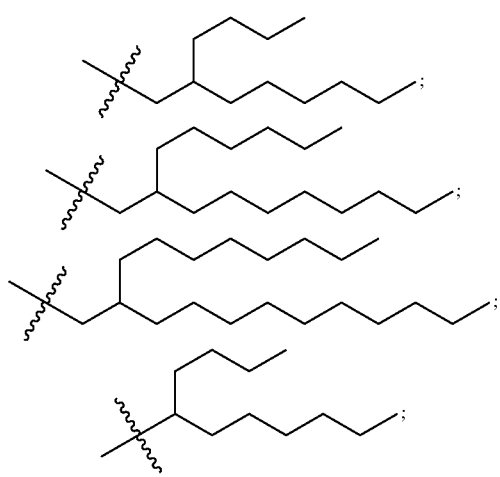

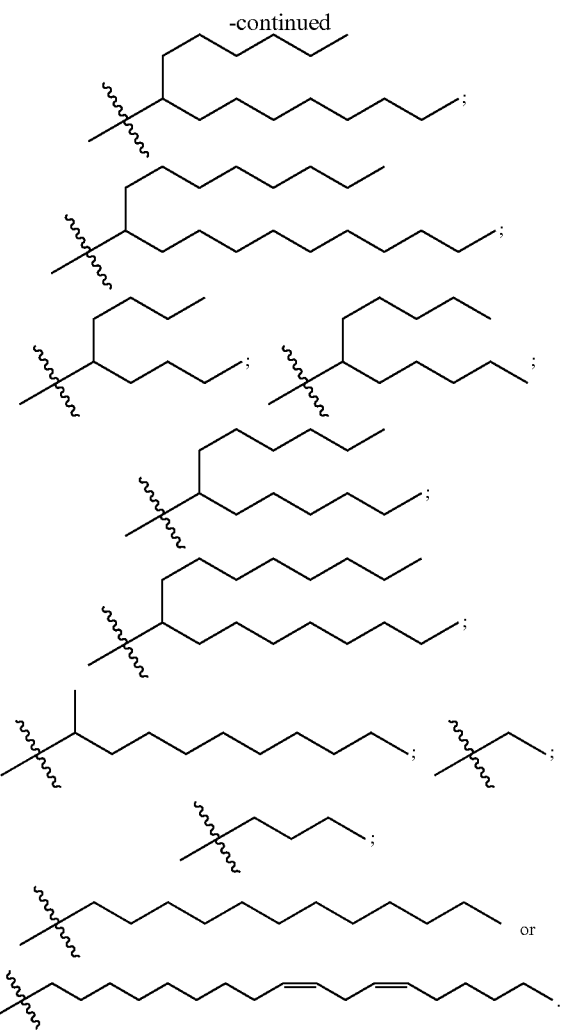

18. The compound of claim 1, having one of the following structures:

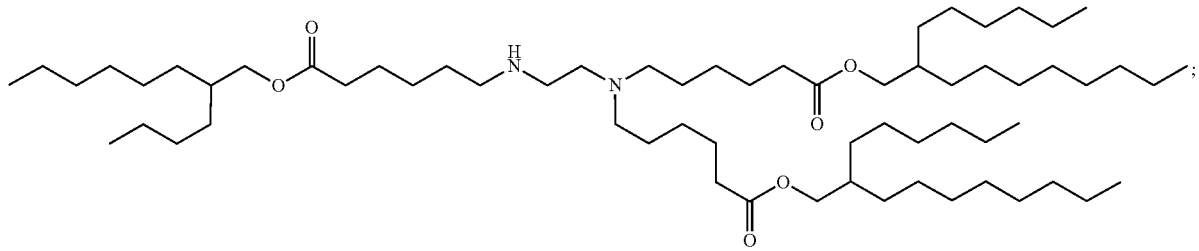

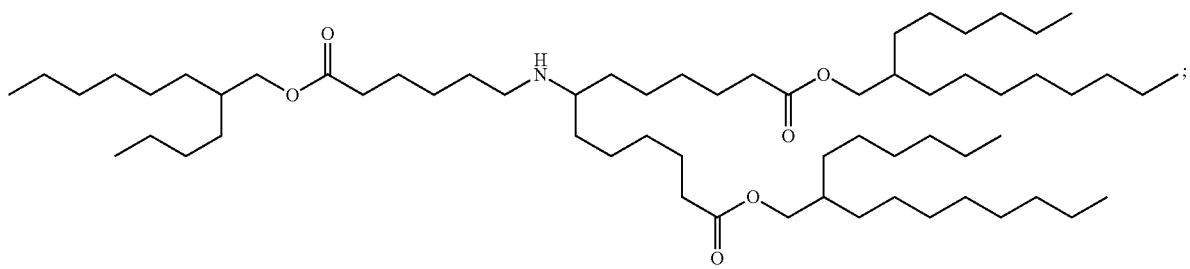

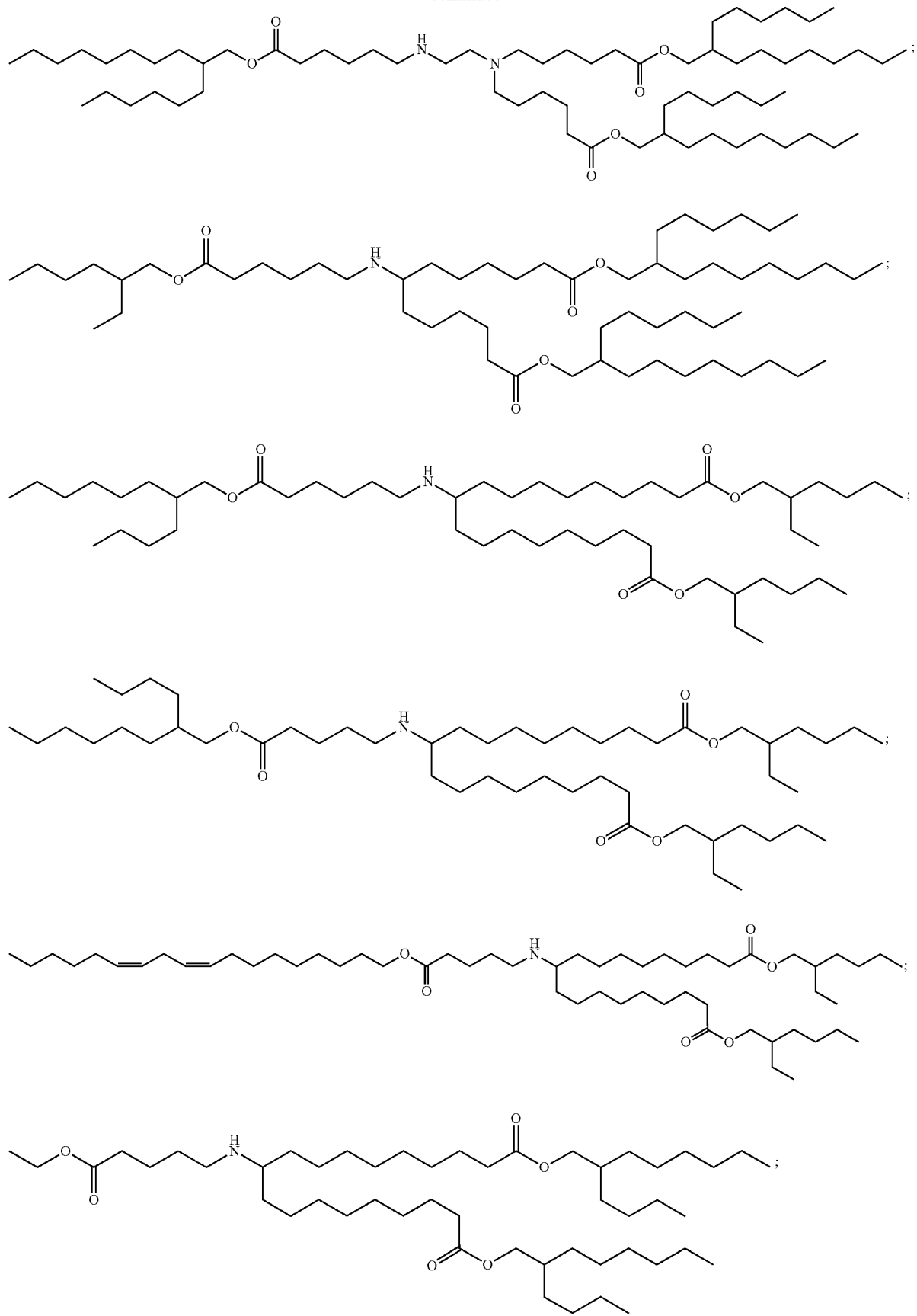

-continued

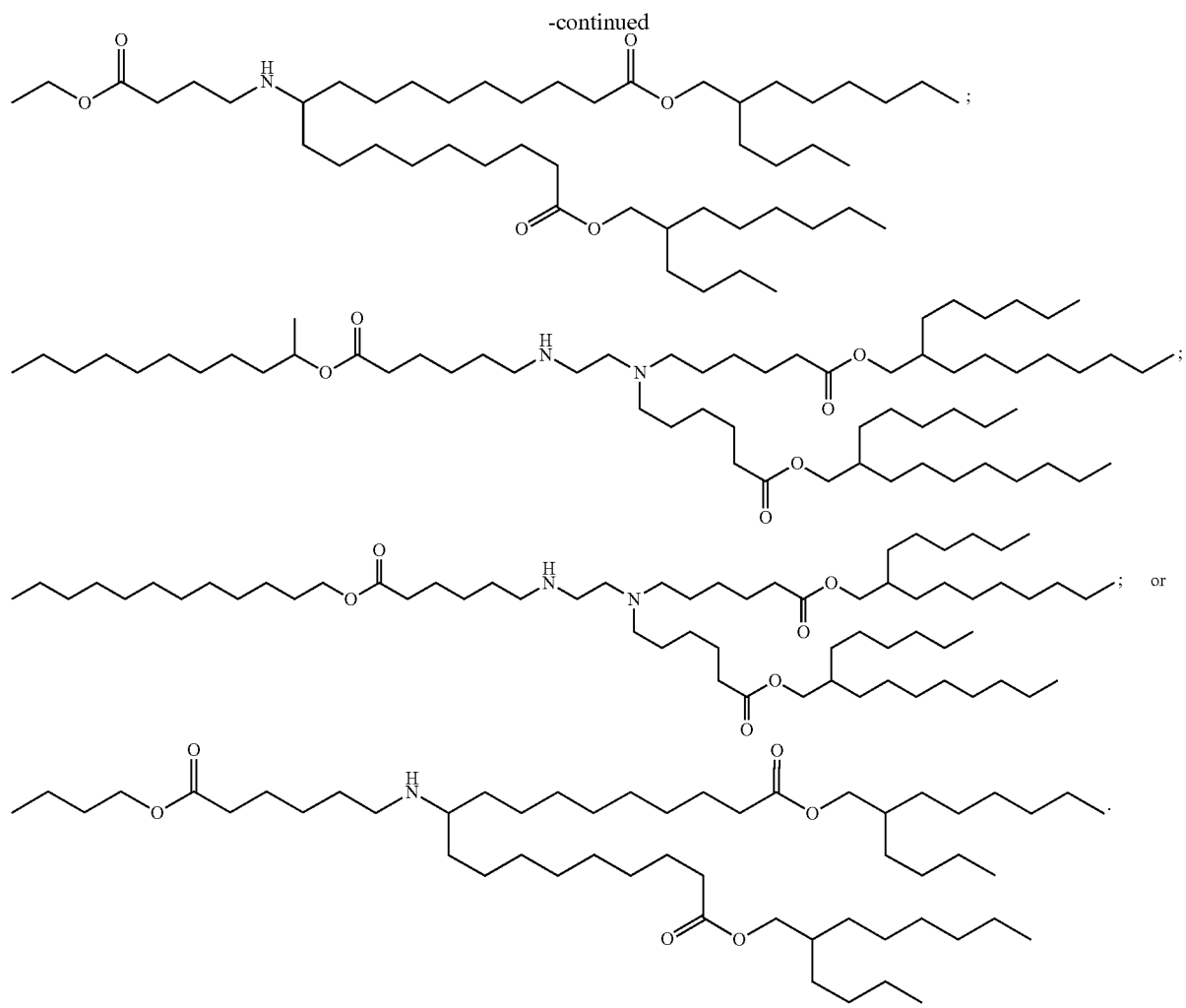

19. A composition comprising the compound of claim 1 and a therapeutic agent.

20. The composition of claim 19, wherein the therapeutic agent comprises a nucleic acid.

21. The composition of claim 20, wherein the nucleic acid is selected from antisense and messenger RNA.

22. A method for administering a therapeutic agent to a patient in need thereof, the method comprising preparing or providing the composition of claim 19, and administering the composition to the patient.

23. A lipid nanoparticle comprising the compound of claim 1.

24. A pharmaceutical composition comprising the lipid nanoparticle of claim 23 and a pharmaceutically acceptable diluent or excipient.

* * * * *